US009528143B2

(12) United States Patent
Ward et al.

(10) Patent No.: US 9,528,143 B2
(45) Date of Patent: *Dec. 27, 2016

(54) TRACER REAGENTS THAT ENHANCE REACTION-PRODUCT ANALYSIS

(75) Inventors: Brian W. Ward, St. Louis, MO (US); David M. Ornitz, Creve Couer, MO (US); Michael G. Deines, Ballwin, MO (US); Thomas F. Bittick, Kirkwood, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/734,616

(22) Filed: Apr. 12, 2007

(65) Prior Publication Data
US 2008/0160518 A1    Jul. 3, 2008

Related U.S. Application Data

(63) Continuation of application No. 11/058,675, filed on Feb. 15, 2005, now abandoned, which is a continuation of application No. 09/610,935, filed on Jul. 6, 2000, now Pat. No. 6,942,964.

(60) Provisional application No. 60/143,009, filed on Jul. 9, 1999.

(51) Int. Cl.
  *C12Q 1/68*  (2006.01)
  *C12Q 1/00*  (2006.01)
  *C12N 9/00*  (2006.01)

(52) U.S. Cl.
  CPC ................... *C12Q 1/6813* (2013.01)

(58) Field of Classification Search
  None
  See application file for complete search history.

(56) References Cited

U.S. PATENT DOCUMENTS

| | | | | |
|---|---|---|---|---|
| 4,879,214 A * | 11/1989 | Kornher | ............... | C12Q 1/6816 435/6.1 |
| 5,407,800 A | 4/1995 | Gelfand et al. | | |
| 5,928,906 A | 7/1999 | Koster et al. | | |
| 6,117,986 A | 9/2000 | Nardone et al. | | |
| 6,153,412 A | 11/2000 | Park et al. | | |
| 6,881,559 B2 * | 4/2005 | Sobek et al. | ................. | 435/91.2 |
| 6,942,964 B1 * | 9/2005 | Ward et al. | ........................ | 435/4 |
| 7,169,584 B2 | 1/2007 | Ward et al. | | |
| 7,195,917 B2 * | 3/2007 | Brown et al. | ................. | 435/468 |
| 2013/0034879 A1 * | 2/2013 | Skirgaila et al. | ............ | 435/91.2 |

FOREIGN PATENT DOCUMENTS

| WO | 96/00301 A1 | 1/1996 |
|---|---|---|
| WO | 97/05273 | 2/1997 |

OTHER PUBLICATIONS

"Visible Spectrum," en.Wikipedia.org, website accessed Mar. 17, 2012.*
Alba, M., et al., "Replicative DNA Polymerases," Genome Biol., 2001, vol. 2, Reviews 3002.1.
Brautigam, C.A., et al., "Structural and Functional Insights Provided by Crystal Structures of DNA Polymerases and Their Substrate Complexes," Current Opinion in Structural Biology, 1998, vol. 8, pp. 54-63.
Hoppe, et al., "Gel-Loading Dyes Compatible with PCR," Bio Techniques, 1992, vol. 12, pp. 679-680.
Jager, J. et al., "Getting a Grip: Polymerases and Their Substrate Complexes," Current Opinion in Structural Biology, 1999, vol. 9, pp. 21-28.
Setterquist et al., "Ready to Use Agarose Encapsulated PCR Reagents," Nucleic Acids Research, 1996, vol. 24 (8), pp. 1580-1581.
Sousa, R., "Structural and Mechanistic Relationships Between Nucleic Acid Polymerases," Trends Biochem Sci, 1996, vol. 21, pp. 186-190.
Advanced Biotechnologies Catalogue No. AB-0406, "Red Hot DNA Polymerase," http://www.advio.co.uk/reagents/rea4.html.
Advanced Biotechnologies Catalogue No. AB-0785, "Thermoprime Plus with ReddyMix Buffer," http://www.advio.co.uk/reagents/rea4.html.
Current Protocols in Molecular Biology, 1988, Supp. 4, pp. 2.5.1-2.5.9, Ausubel, F.M. Editor, Greene Publishing Associates, NY.
Hingorani, M.M., et al., "DNA Polymerase Structure and Mechanisms of Action," http://www.bentham.org/coc-sample/o-donnell/o-donnell.html.
Molecular Cloning a Laboratory Manual, Second Edition, 1989, pp. 5.28-5.31, Sambrook, Fritsch and Maniatis, Eds., Cold Spring Harbor Laboratory Press, NY.
Origene Technologies, Inc. Catalogue No. RL-104, "Rapid-Load", http://www.origene.com/redi.htm.
Research Genetics Catalogue No. 750025, "RediLoad," http://www.resgen.com/products/RedLpf.php3.
Slickers, P., "DNA Polymerases," http://www.imb-jena.de/~slickers/polymerases/dna-polymerases.html.

(Continued)

*Primary Examiner* — Bradley L Sisson

(57) ABSTRACT

A composition suitable for formulation of an enzymatic reaction mixture, the composition comprising a reaction component essential for an ex-vivo non-polymerase enzymatic reaction in which a substrate is catalyzed by an enzyme in a reaction mixture to form a product, and a tracer compatible with the enzyme, the composition being substantially free of the substrate.

10 Claims, 18 Drawing Sheets

(56) References Cited

OTHER PUBLICATIONS

Weglarz-Tomczak et al., "Azo dyes—biological activity and synthetic strategy," CHEMIK, 2012, pp. 1298-1307, vol. 66, No. 12.
Glover, "Doing what comes naturally in the dyehouse," Journal of the Society of Dyers and Colourists, 1998, pp. 4-7, vol. 114, No. 1.

* cited by examiner

FIG. 4

PHYSICAL CHARACTERISTICS (e.g. HIGH DENSITY TO ENABLE GEL LOADING, COLORED TO VISUALIZE GEL LOADING, ANIONIC CHROMOPHORE TO TRACK ELECTROPHORESIS PROGRESS, COLOR (IF DESIRED)).

ASSEMBLE COLLECTION OF REAGENTS FOR SCREENING (e.g. COLLECT A LARGE SAMPLING OF ANIONIC DYES).

SCREEN MOLECULES FOR COMPATIBILITY. THE SCREENING MIGHT BE BEST CARRIED OUT BY PRIORITIZING THE DESIRED PROPERTIES FROM LEAST TO MOST LABORIOUS (e.g. SEE RED Taq SCHEME 5).

FORMULATE REAGENT, CHARACTERIZE REACTION PRODUCTS (QUALITATIVE AND QUANTITATIVE). OPTIMIZE OTHER REACTION COMPONENTS FOR PERTURBATION (IF NECESSARY). FINAL CHARACTERIZATION (REACTION PRODUCT QUALITY AND QUANTITY) AND LIMITATIONS (e.g. INCOMPATIBLE WITH SPECIFIC DOWNSTREAM APPLICATIONS).

FIG. 5

PHYSICAL CHARACTERISTICS
HIGH DENSITY TO ENABLE GEL LOADING-FORMULATE ENZYME DILUTE ENOUGH SO THAT ENOUGH GLYCEROL WILL BE CONTAINED IN A 2.5 UNIT PER 50 MICROLITER REACTION.
COLORED TO VISUALIZE GEL LOADING AND ACT AS A TRACKING DYE-RED ANIONIC WATER AND ETHANOL SOLUBLE DYES WERE SOUGHT.

↓

ASSEMBLE COLLECTION OF REAGENTS FOR SCREENING-40 ANIONIC "RED" (LAMBDA MAX=450-550) DYES WERE SELECTED AS CANDIDATES.

↓

SCREEN MOLECULES FOR COMPATIBILITY-SUMMARIZED IN FIGURE 1. THE DYES WERE SCRUTINIZED IN THE ORDER:
1. COLOR (TOO YELLOW OR PURPLE THROWN OUT)
2. ETHANOL PRECIPITATION (COLORED DNA PELLETS THROWN OUT).
3. CHAOTROPIC SALT/SILICA DNA PURIFICATION (COLORED PRODUCT THROWN OUT).
4. PCR TOXICITY (FIGURE 2, LOW OR NO YIELD THROWN OUT).
5. LIGASE TOXICITY (FIGURE3, LOW OR NO YIELD THROWN OUT).
6. TRANSFORMATION TOXICITY (FIGURE 4, LOW OR NO YIELD THROWN OUT).
7. REMAINING DYES MORE OR LESS EQUIVALENT, SUBMIT TO MARKETING FOR COLOR SELECTION.

↓

FORMULATE REAGENT-80% ACID RED 1, 20% ACID VIOLET 5 (100%=ABSORBANCE OF ACID RED 1 AT LAMBDA MAX+ABSORBANCE OF ACID VIOLET 5 AT LAMBDA MAX.) TO ABSORBANCE TOTAL=300 IN Taq DNA POLYMERASE AT 1 UNIT PER MICROLITER IN Taq STORAGE BUFFER (20 mM Trs-HCL, pH 8.0, 100 mM KCl, 0.1 mM EDTA, 1 mM DTT, 0.5% TWEEN 20, 0.5% Igepal CA-630, 50% GLYCEROL).
CHARACTERIZE REACTION PRODUCTS-PRODUCT YIELDS LOW RELATIVE TO ABSENCE OF DYE REACTIONS (FIGURE 5). DYE PURITY (FIGURE 6) AND COUNTER ION IDENTITY (FIGURE 7) INVESTIGATED FOR PCR TOXICITY/COMPATIBILTY. PURIFIED Mg ACID RED 1 AND Mg ACID VIOLET 5 FOUND TO BE SATISFACTORY.
OPTIMIZE OTHER REACTION COMPONENTS-Mg DYES CONTRIBUTE APPROXIMATELY 0.4 mM "FREE" Mg TO PCR (FIGURE 8), 10X PCR BUFFER ADJUSTED FROM 15 TO 11 mM TO ACCOMODATE Mg DYE CONTRIBUTION.
FINAL CHARACTERIZATION-QUALITY: GEL (FIGURE 9), QUANTITY (FIGURE 10). LIMITATIONS-WILL TEST WITH A PANEL OF RESTRICTION ENZYMES, DOES NOT IMPACT FLUORESCENT SEQUENCING.

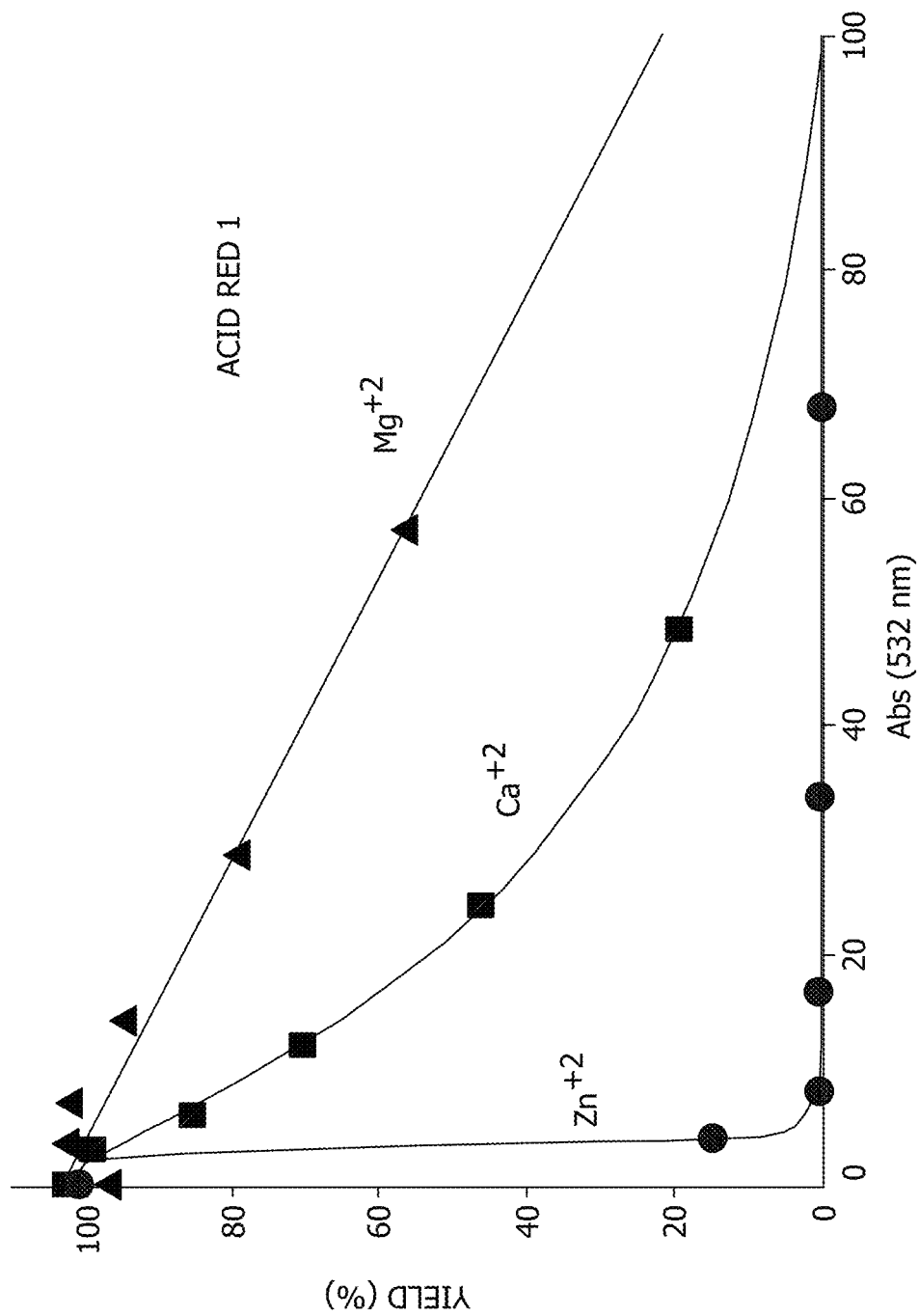

TRACER REAGENTS THAT ENHANCE REACTION-PRODUCT ANALYSIS

CROSS REFERENCE TO RELATED APPLICATIONS

This application is a continuation of U.S. patent application Ser. No. 11/058,675, filed Feb. 15, 2005, which is a continuation of U.S. patent application Ser. No. 09/610,935, filed Jul. 6, 2000, now issued as U.S. Pat. No. 6,942,964, which claims priority from U.S. Provisional Patent Application Ser. No. 60/143,009, filed Jul. 9, 1999, the content of each of which is hereby incorporated herein by reference.

BACKGROUND OF THE INVENTION

The present invention generally relates to reagents that are essential for an enzymatic reaction and that enhance reaction-product analysis. In specific, preferred embodiments, the invention provides compositions of essential components which facilitate subsequent chromatographic or electrophoretic analysis.

Enzymes are frequently used in laboratories to catalyze a variety of transformations. Typical enzymes which have been utilized include proteases, peroxidases, oxidases, kinases, amylases, and several nucleic acid modifying enzymes such as DNA polymerases, RNA polymerases, ligases, kinases, restriction endonucleases, phosphodiesterases, DNases, exonucleases, RNases, and phosphatases. The nucleic acid-modifying enzymes have been frequently used in molecular biology laboratories as part of procedures such as polymerase chain reaction ("PCR"), sequencing, southern hybridization analysis, restriction endonuclease analysis, RNase protection, and the production of labeled probes The steps involved in performing an enzyme catalyzed transformation can generally be categorized as reaction mixture formulation, enzymatic reaction, reaction product characterization, and reaction product use. The steps of mixture formulation, product characterization, and product use are labor intensive. The formulation of enzyme reaction mixtures entails combining reaction components which are essential for the enzymatic reaction into a reaction mixture. The reaction mixture is then incubated under conditions favorable for the enzymatic reaction to take place, and for a time sufficient to allow the enzymatic reaction to proceed substantially to completion. The reaction mixture is typically analyzed to evaluate the characteristics of the products formed. This analysis often entails a chromatographic or electrophoretic procedure to separate and evaluate the reaction products, and to determine whether the enzymatic reaction has proceeded to completion. Downstream applications entail a wide variety of varied uses for the products of enzymatic reactions, such as utilization in manufacturing, and further processing of the product with enzymes or chemical processes. In the case of molecular biological enzymatic reactions, examples of downstream applications are transformation of prokaryotic or eukaryotic cells, detection of complementary sequences by southern or northern hybridization, sequencing, phosphorylation, dephosphorylation, ligation, restriction digestion, endonucleolytic digestion, exonucleolytic digestion, and purification.

Procedures such as liquid chromatography and polyacrylamide gel electrophoresis ("PAGE") have been frequently used to analyze the results of the enzymatic reactions by separating the reaction products by, for example, molecular weight. The results of the modification of nucleic acids by enzymes such as DNA polymerase have typically been analyzed by subjecting the reaction products to electrophoresis through polyacrylamide or agarose gels.

To analyze enzymatic reaction products using chromatography or electrophoresis, the sample to be analyzed has often been combined with components which assist the operator in performing the separation. One such component is a "tracer", which is a detectable moiety such as a dye which is generally added to the sample immediately before loading the sample onto the chromatography column or electrophoresis gel. The tracer migrates in the medium in the same direction as the sample to indicate the progress of the separation.

Another reagent, termed "high density agent" herein, has also been commonly utilized in electrophoretic analysis of the enzymatic reaction products. High density agents are generally water soluble, dense liquids, such as a solution of sucrose or glycerol, which have been mixed with the sample, usually after the enzymatic reaction is complete, to increase the sample density. The increased density of the sample resulting from mixing the sample with the high density agent aids, for example, in loading the sample into a well of an electrophoresis gel by allowing the sample, when pipetted into the top of the well, to "fall" through the less-dense electrophoresis buffer solution to the bottom of the well.

High density agent and tracer have been combined with reaction product-containing samples to be electrophoretically separated. The combination of high density agent and tracer is generally termed "loading buffer".

While tracers and loading buffers have usually been mixed with the sample after the enzymatic reaction is complete, as diagramed in FIG. 1, their use before the commencement of nucleic acid-modifying enzymatic reactions is also known, as diagramed in FIG. 2. Hoppe et al., BioTechniques 12:679-680 (1992) describe combining a solution of sucrose (up to 30%) and certain dyes (cresol red, tartrazine, or yellow food coloring #5) with an enzyme reaction mixture containing all other components for PCR. After the PCR procedure, the samples were reportedly loaded directly onto an agarose gel for electrophoretic analysis. The authors noted that several dyes and heavy components were inhibitory to the Taq polymerase enzyme used, but that sucrose, cresol red, tartrazine, and yellow food coloring #5 were compatible with Taq.

Certain commercially available products provide tracer or loading buffer for use in enzyme reaction mixes for PCR. A thermostable polymerase preparation, RED HOT® DNA Polymerase, is available from Advanced Biotechnologies and reportedly contains a red dye for use to indicate enzyme addition in the enzyme reaction mixture. There are also two products available which comprise a red tracer and a high density agent, for addition to a PCR reaction mixture before amplification. One, called REDILOAD™, is available from Research Genetics, Inc., and the other, called RAPID-LOAD™, is available from OriGene Technologies. These reagents must be added to the reaction mixture in a separate pipetting step.

SUMMARY OF THE INVENTION

Despite the efforts and improvements made in the prior art, inefficiencies in reaction mixture formulation and reaction product analysis still exist. In particular, there is no product to date which combines an essential component for an enzyme reaction with a tracer and/or high density agent which can be used in an enzymatic reaction and provide sufficient tracer and/or high density agent such that the product of the enzyme reaction could be directly evaluated in a chromatographic or electrophoretic procedure without supplying additional tracer or high density agent. Such a product ("analysis reagent composition") would provide additional advantages over the products currently available because it would (1) indicate reagent addition into the enzymatic reaction mix, and (2) eliminate the need for separately adding a loading buffer since the loading buffer components are added along with the essential reagent.

Among the several objects of the invention, therefore, is the provision of compositions for use in formulating enzymatic reaction mixtures that offer improved efficiencies in connection with the labor intensive protocols for reaction mixture formulation, and reaction product characterization.

The invention is thus generally directed to the provision of a composition comprising an essential component of an enzymatic reaction combined with a tracer which is compatible with the enzyme, where the composition contains an essential absence of the substrate. The composition can have a density at least about 1.01 $g/cm^3$. This composition is particularly useful for any enzyme reaction where post-reaction processing or analysis is benefited by the tracer and/or increased density of the reaction mixture. In particular, such compositions for polymerase and restriction enzyme reactions are provided, where the presence of the tracer and/or increased density is useful for post-reaction electrophoretic analysis. Methods for using these compositions, and methods for preparing these compositions are also provided.

The invention is directed, therefore, to a composition which is suitable for formulation of an enzymatic reaction mixture, the composition comprising a reaction component essential for an ex-vivo non-polymerase enzymatic reaction in which a substrate is catalyzed by an enzyme in a reaction mixture to form a product, and a tracer compatible with the enzyme, wherein the composition is substantially free, or has an essential absence, of the substrate. These compositions can further comprise a density of at least about 1.01 $g/cm^3$.

The present invention is also directed toward a composition comprising a reaction component essential for an ex-vivo enzymatic reaction in which a substrate is catalyzed by an enzyme in a reaction mixture to form a product and a tracer compatible with the enzyme, the composition being substantially free or having an essential absence of the substrate and having an optical density greater than about 5 at a visible wavelength of maximal tracer absorbance.

The present invention is further directed toward a composition comprising a reaction component essential for an ex-vivo polymerase reaction in which a nucleic acid polymer product complementary to a nucleic acid polymer template is prepared, and a tracer compatible with the polymerase, the composition being substantially free or having an essential absence of the template and has an optical density greater than about 5 at a visible wavelength of maximal tracer absorbance. These compositions can also comprise a density of at least about 1.01 $g/cm^3$.

The present invention is still further directed toward a composition for an enzymatic reaction component which comprises a reaction component essential for an ex-vivo enzymatic reaction in which a substrate is catalyzed by an enzyme in a reaction mixture to form a product, and an alkaline earth-metal salt of an anionic tracer.

The present invention is also directed toward a composition which comprises a reaction component essential for an ex-vivo enzymatic reaction in which a substrate is catalyzed by an enzyme in a reaction mixture to form a product, and a tracer selected from the group consisting of acid red 106, acid red 4, acid red 1, amaranth, and acid violet 5, or a salt thereof.

The present invention is further directed toward a composition comprising a reaction component essential for an ex-vivo enzymatic reaction in which a nucleic acid polymer substrate is enzymatically cleaved by a restriction enzyme in a reaction mixture to form a restriction product, and a tracer compatible with the restriction enzyme, wherein the composition contains an essential absence of the substrate. These compositions can also comprise a density of at least about 1.01 $g/cm^3$.

The present invention is still further directed toward an improvement in a method for a polymerase reaction that comprises forming a reaction mixture comprising a polymerase, a nucleic acid polymer template, a tracer compatible with the polymerase, and other components essential for the polymerase reaction, creating a nucleic acid polymer product complementary to the nucleic acid by enzymatic reaction, analyzing the product of the enzymatic reaction by an electrophoretic protocol, and observing the tracer during the electrophoretic protocol without providing additional tracer beyond that which was included in the reaction mixture. The improvement comprises supplying the tracer to the reaction mixture in a composition that comprises the tracer and the enzyme or another essential component, the composition being substantially free or having an essential absence of the nucleic acid polymer template. A further improvement is in the reaction mixture having a density at least about 1.01 $g/cm^3$.

The present invention is further directed toward an improvement in a method for a polymerase reaction that comprises forming a reaction mixture comprising a polymerase, a nucleic acid polymer template, a tracer compatible with the polymerase, and other components essential for the polymerase reaction, creating a nucleic acid polymer product complementary to the nucleic acid by enzymatic reaction, analyzing the product of the enzymatic reaction by an electrophoretic protocol, and observing the tracer during the electrophoretic protocol. The improvement comprises supplying the tracer to the reaction mixture in a composition that comprises the tracer and the enzyme or another essential component, the composition being substantially free or having an essential absence of the nucleic acid polymer template, wherein the tracer supplied to the reaction mixture is of adequate character and sufficient quantity to be visible during the electrophoretic protocol.

The present invention is also directed toward a method for a restriction enzyme reaction, the method comprising forming a reaction mixture comprising a restriction enzyme, a nucleic acid polymer substrate, a tracer compatible with the restriction enzyme, and other components essential for the enzymatic reaction, enzymatically cleaving the nucleic acid polymer substrate to form a restriction product, analyzing the product of the cleavage reaction by an electrophoretic protocol, and observing the tracer during the electrophoretic protocol without providing additional tracer beyond that which was included in the reaction mixture. The density of the reaction mixture can also be at least about 0.01 g/cm greater than the liquid phase utilized in the chromatographic or electrophoretic protocol.

The present invention is also directed toward a method for a restriction enzyme reaction, the method comprising forming a reaction mixture comprising a restriction enzyme, a nucleic acid polymer substrate, a tracer compatible with the restriction enzyme, and other components essential for the enzymatic reaction, enzymatically cleaving the nucleic acid polymer substrate to form a restriction product, analyzing the product of the cleavage reaction by an electrophoretic protocol, wherein the tracer supplied to the reaction mixture is of adequate character and sufficient quantity to be visible during the electrophoretic protocol.

The present invention is further directed toward a method for forming an enzymatic composition, the method comprising combining a reaction component with a tracer, the reaction component being essential for an enzymatic reaction in which a substrate is catalyzed by an enzyme in a reaction mixture to form a product, the tracer being compatible with the enzyme, and the resulting composition having an optical density greater than about 15 at a visible wavelength of maximal tracer absorbance. A liquid which is compatible with the enzyme can also be added, wherein the liquid increases the density of the composition to at least about 1.1 g/cm$^3$.

The present invention is still further directed toward a method for forming an enzymatic composition, the method comprising combining a reaction component with a tracer, the reaction component being essential for a polymerase reaction in which a nucleic acid product is polymerized from a complementary nucleic acid template, the tracer being compatible with the enzyme, and the resulting composition having an optical density greater than about 5 at a visible wavelength of maximal tracer absorbance. A liquid which is compatible with the enzyme can also be added, wherein the liquid increases the density of the composition to at least about 1.1 g/cm$^3$.

Other features, objects and advantages of the present invention will be in part apparent to those skilled in the art and in part pointed out hereinafter. All references cited in the instant specification are incorporated by reference. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 4 is a schematic of an enzymatic reaction useful for evaluating the compatibility and effectiveness of a tracer and/or high density agent ("loading buffer component").

FIG. 5 is a schematic summarizing steps that may be taken to develop a composition as described in Example 1.

FIGS. 12A-12C graphically depict PCR yields as affected by either reverse phase desalting of the dyes or ammonium hydroxide dissolution/evaporation of the dyes according to experiments performed in Example 1.

DETAILED DESCRIPTION OF THE PREFERRED EMBODIMENTS

The present invention provides compositions comprising an essential component to an enzyme reaction and a tracer which can allow post-reaction analysis without further tracer addition. These compositions ("analysis reagent compositions") can also comprise a high density agent which can eliminate the need for further addition of a high density agent during post-reaction analysis. Methods of using these compositions, and methods of preparing them are also provided.

Figure 1:
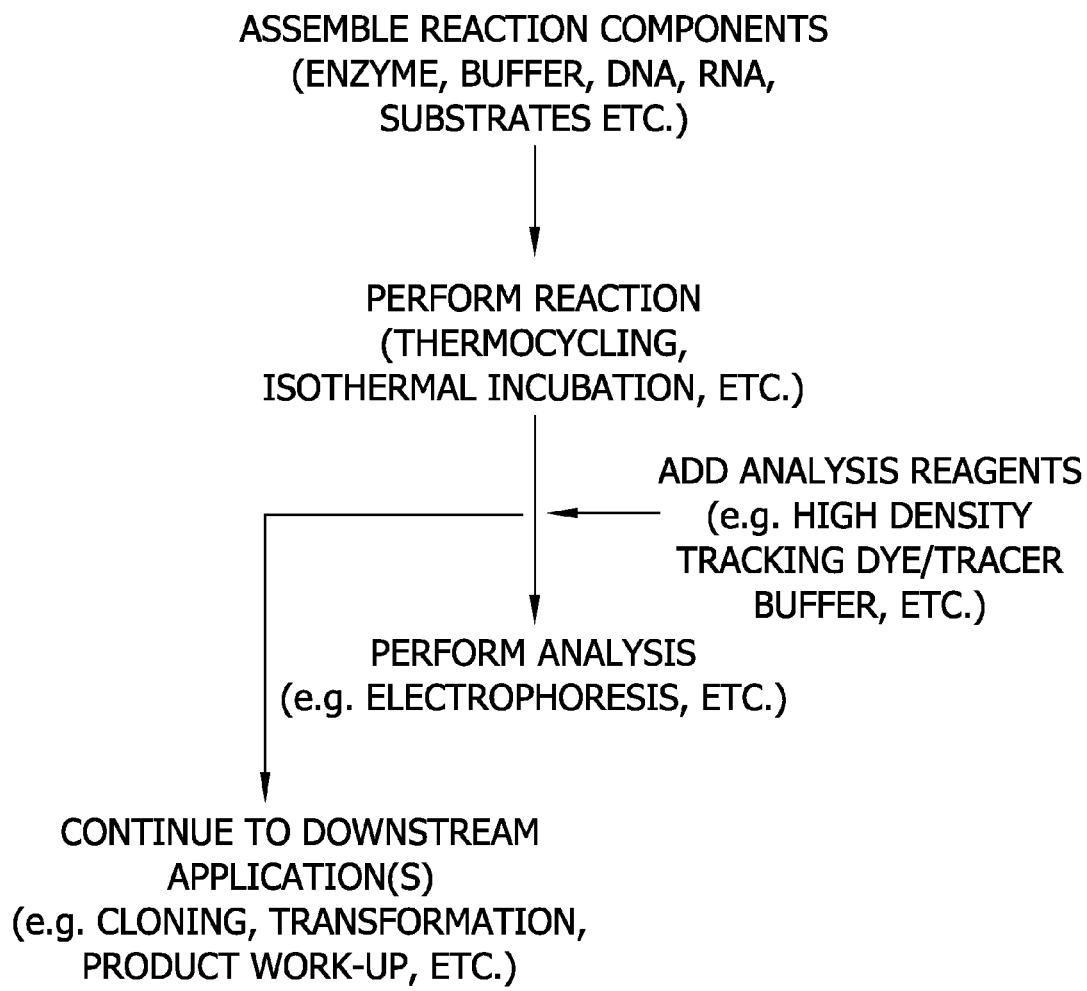
FIG. 1 is a schematic of an enzymatic reaction in which tracers and loading buffers are mixed with the sample after the enzymatic reaction is complete.
Figure 2:
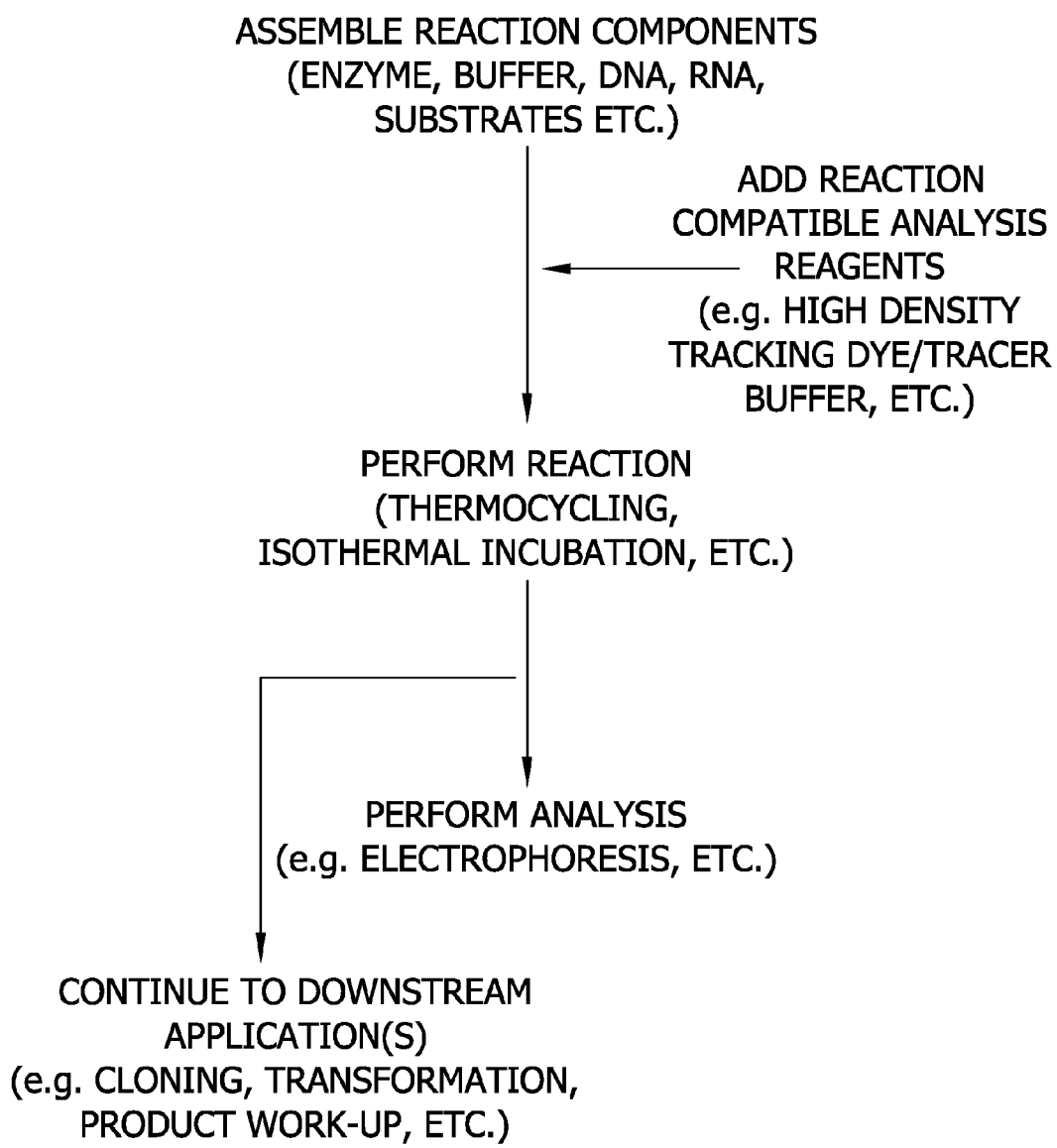
FIG. 2 is a schematic of an enzymatic reaction in which tracers and loading buffers are mixed with the sample before commencement of the enzymatic reaction.
Figure 3:
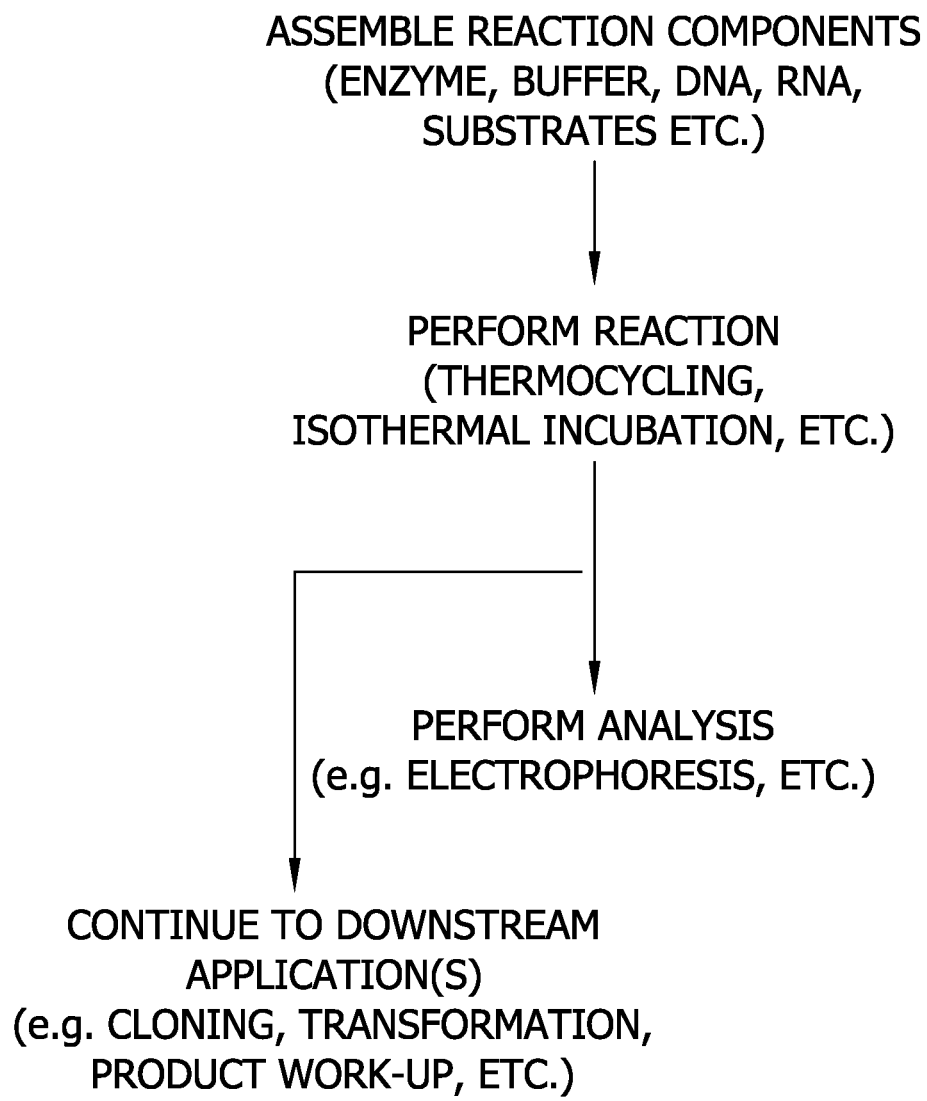
FIG. 3 is a schematic of an enzymatic reaction in which the additional step of adding tracers and loading buffers is eliminated.

Prior art methods of using loading buffer components always added these components to the reaction mixture, either before or after the enzymatic reactions are executed. Such methods require an extra step to add the loading buffer components. An improvement over the prior art in the present invention is the provision of analysis reagent compositions comprising an essential component for an enzymatic reaction combined with the loading buffer components. As diagrammed in FIG. 3, the approach of the present invention offers further efficiencies that were not achieved with prior art protocols. The loading buffer components are passively added with the essential component, thus eliminating the extra addition step required in the prior art to add the loading buffer. In laboratories where many enzyme reaction mixtures are prepared, the compositions and methods of the present invention can thus eliminate a considerable amount of work. These analysis reagent compositions are particularly useful for molecular biological enzyme reactions, particularly polymerase reactions and restriction enzyme reactions, since these reactions are often repetitively performed under standardized conditions.

The procedures disclosed herein which involve the molecular manipulation of nucleic acids are known to those skilled in the art. See generally Joseph Sambrook et al. (1989), "Molecular Cloning, A Laboratory Manual", second ed., Cold Spring Harbor Laboratory Press.

As used herein, the term "substrate" encompasses a component of an enzymatic reaction mixture which is a reactant in the reaction catalyzed by the enzyme. For example, in a restriction enzyme reaction, the substrate is the nucleic acid polymer which is cut by the enzyme. In a polymerase chain reaction, the substrates include the primer which is extended by the enzyme, and the nucleotides which are added to the growing nucleic acid polymer.

The present invention provides compositions comprising a reagent which is essential for an enzymatic reaction ("essential reagent") and a tracer which is compatible with the enzyme. A high density agent may also be included in these compositions. Methods are also provided wherein the compositions are used in an enzymatic reaction and the results are subsequently analyzed by electrophoresis or chromatography in a water soluble solvent.

The compositions and methods of the present invention are useful in conjunction with any enzymatic reaction where the reaction products are subsequently analyzed by a chromatographic or electrophoretic method. Enzymes which can be employed include those which modify or degrade proteins, lipids, carbohydrates, and metabolites, such as any kinase, protease, lipase, amylase, peroxidase, oxidase, oxygenase, and dehydrogenase. Enzymes which modify, cut, or synthesize nucleic acids are particularly suitable to be used with the present invention. Examples include any ligase, phosphodiesterase, DNase, exonuclease, RNase, phosphatase, kinase, terminal transferase, reverse transcriptase, restriction endonuclease, RNA polymerase, and DNA polymerase. Enzymes which are preferred for use with this invention are restriction endonucleases and DNA polymerases. More preferred are DNA polymerases; even more preferred are any thermostable DNA polymerase; most preferred is wild-type or modified Taq polymerase. These enzymes can be in any concentration which is useful for performing an enzymatic reaction. Preferred concentrations of Taq polymerase in the compositions of the present invention are 0.033-10 units/µl, more preferred concentrations are 0.06-5 units/µl, the most preferred concentration is 1 unit/µl. Preferred concentrations of restriction endonucleases in the compositions of the present invention are 0.1-1000 units/µl, more preferred concentrations are 1-100 units/µl, most preferred concentrations are 5-40 units/µl.

Tracers which can be used in this invention include detectable compounds which can be incorporated into the reaction mixture and not interfere significantly with the enzyme reaction. Such a tracer is designated herein as "compatible" with the enzyme. It is preferred that this compatibility be such that an enzyme composition with the tracer has at least 95% of the activity of the same composition without the tracer. More preferably, the tracer-enzyme composition has at least about 97% activity of the composition without the tracer, even more preferably at least about 99% activity, and most preferably about 100% activity. The tracer should also be stable enough in the tracer-enzyme composition to retain its compatibility with the enzyme even after a long storage period at an appropriate temperature, e.g. 1 year or more at −20° C.

The detectable signal imparted by the tracer can be visual, such as that imparted by a dye or fluorescent compound. The tracer can also impart a radioactive, electrochemical, spectrophotometric, or any other type of signal which can be detected sensually or with an instrument and which can serve as a useful marker in an analysis subsequent to the enzyme reaction. Preferred are tracers which impart a visual signal. The most preferred tracers are dyes which are colored under the conditions that the analysis is performed. Any color dye which is visible during the post-reaction analysis can be used; preferred are dyes which have a peak visible absorbance wavelength at between 430 and 617 nm; most preferable dyes have a peak visible absorbance wavelength at between 500 and 535 nm.

While any tracer compatible with the enzyme can be useful in the present invention, preferred tracers are highly soluble in the liquid phase of the post-reaction chromatographic or electrophoretic procedure. The tracer is preferably an anionic tracer. Particularly preferred tracers are anionic tracers such as salts of organic acid dyes or sulfonic acid dyes. The preferred salt counterion is an earth metal, most preferably $Ca^{++}$ or $Mg^{++}$. Where the post-reaction analysis is an electrophoresis of a nucleic acid, preferred tracers are anionic dyes. Preferred concentrations of the tracer in an analysis reagent composition are concentrations for which the composition has an optical density (OD) of between about 5 and about 500; most preferred is about 300. In enzyme reaction mixtures prepared from the analysis tracer composition the preferred tracer concentration has an OD of between 1 and 100; more preferred is 15 to 50; most preferred is 15.

Commercial preparations of tracers are often inhibitory to enzyme activity when used in the concentrations recited above. This inhibition can often be overcome by further purification of the tracer, for example by reverse phase desalting, recrystalization, acid precipitation, or chromatographic methods such as reverse phase, normal phase, or ion exchange chromatography. Where the tracer is an anion, such as disclosed in Example 1 below, enzyme inhibition can also be overcome by replacing the counterion with an alkaline earth-metal. Preferred alkaline earth-metals for this purpose are $Ca^{++}$ and $Mg^{++}$; most preferred is $Mg^{++}$.

High density agents useful for the present invention include any solute in which the tracer is soluble and which is compatible with the enzyme when diluted in the final reaction mixture, and which is dense enough to assist in the addition of reaction mixture to the analytical process. To provide such assistance, the density of the reaction mixture should be at least about 0.01 g/cm$^3$ greater than the density of the liquid phase of the analytical process (e.g. the electrophoresis or chromatographic buffer). A somewhat higher density (for example, about 0.05 g/cm$^3$ greater than the analytical liquid phase) would provide greater assistance in the addition of the reaction mixture, and is thus more preferred. These densities may be provided using the preferred density of an essential enzyme component/tracer/high density agent composition of about 1.14 g/cm$^3$. Higher densities are also useful, however, provided they are compatible with the enzyme at the concentration used in the enzyme reaction.

Examples of solutes which are generally compatible with enzymes at the concentrations required to provide sufficient density are sucrose or other sugars, glycerol, and betaine (trimethylglycine). Glycerol is preferred. Glycerol at a concentration of 1.5% in water is about 0.01 g/cm$^3$ more dense than water, and would thus provide assistance in applying a sample to an analytical process where water is the liquid phase. Glycerol at a concentration of 50% in water has a density of about 1.14 g/cm$^3$. Thus, 50% glycerol is preferred as the high density agent in an essential enzyme component/tracer/high density agent composition.

A scheme which is useful for evaluating the compatibility and effectiveness of a tracer and/or high density agent ("loading buffer component") for this invention is shown in FIG. 4. In this scheme, the desired physical characteristics of the loading buffer component is determined. For example, the desired color and charge of a dye to be used as a tracer is decided. Next, a set of candidates (e.g. red, anionic dyes) is assembled for testing to evaluate other desired properties (e.g. enzyme compatibility, lack of interference in genetic transformation protocols, etc). The candidates are then tested for these desired properties, preferably by performing the least laborious tests first, in order for the largest amount of undesirable candidates to be eliminated by the least amount of screening. When desirable loading buffer components are selected, the formulation of loading buffer component and essential reagent is prepared, and its effect on the enzyme reaction and subsequent analysis is characterized.

Any essential reagent can be selected to be combined with the loading buffer component to formulate a composition of the present invention. The selection of an essential reagent for this purpose can depend on factors such as:

whether it is desired to be able to determine if the essential reagent has been added to the enzyme reaction mixture. For example, if the essential reagent is an enzyme and the loading buffer component is a dye, then one can easily determine if the enzyme has been added to the reaction mixture by determining if the reaction mixture is colored.

whether the essential reagent might be added at varying concentrations in several reaction mixtures, or whether there are alternative formulations of essential reagents which might be added. For example, a particular buffer solution can be used at different concentrations by several different restriction endonucleases. See Joseph Sambrook et al. (1989), "Molecular Cloning, A Laboratory Manual", second ed., Cold Spring Harbor Laboratory Press, at pp. 5.28-5.31. The concentrated buffer solution may not be a preferred essential reagent to combine with the loading buffer components under those conditions, since the final reaction mixtures could have varying concentrations of the loading buffer components, depending on the enzyme used. However, where the concentrated buffer solution is generally always diluted a particular amount, such as with 10× buffers which are often provided for particular enzymes (e.g. restriction enzymes), the loading buffer components can be usefully provided in combination with these solutions.

Examples of essential reagents which can be combined with loading buffer components to formulate a composition of the present invention are: enzyme, concentrated enzyme buffer (e.g. 10× buffer), a nucleotide or primer reagent in the case of DNA or RNA polymerases, or a coenzyme such as NADPH or ATP. The preferred essential agent for this purpose is the enzyme, since it is often desirable to be able to ascertain if enzyme addition has taken place, and since enzyme concentrations in reaction mixtures are generally not widely varied. A colored enzyme formulation also has the advantage of allowing one to determine if complete mixing of the enzyme has taken place. If the solution is uniformly colored then the enzyme is uniformly distributed. Also, since a colored formulation is more readily visible than a clear formulation, a colored enzyme formulation also facilitates pipetting of the small volumes of enzyme which are often added to enzymatic reaction mixtures.

Inclusion of loading buffer components with the substrate is usually not preferred because the substrate composition and concentration often varies between individual enzyme reactions. For a PCR reaction, however, the loading buffer components can be advantageously added with the nucleotide substrates, since the concentration of these reagents generally do not vary between individual PCR reactions.

As contemplated by the present invention, the analysis of the product of an enzyme reaction can be by any method which is suitable for the product in question. Chromatographic and electrophoretic methods are particularly suitable. Suitable chromatographic methods include liquid chromatography ("LC"), particularly gel permeation chromatography. In LC, a high density agent would facilitate the loading of the reaction mixture containing the product onto a chromatographic column, and a visible tracer would allow one to follow the progression of the sample through the column.

For applications where the product to be analyzed is a nucleic acid polymer, electrophoretic methods are preferred. In this regard, the compositions and methods of the present invention are useful for agarose gel electrophoresis (e.g. to analyze products of PCR, restriction endonuclease digestion, ligation reactions, etc), and polyacrylamide gel electrophoresis (e.g. analysis of sequencing reactions). Polyacrylamide gel electrophoresis is also facilitated by the present invention when used to analyze protein products of enzymatic reactions.

The following examples illustrate the invention, but are not to be taken as limiting the various aspects of the invention so illustrated.

EXAMPLE 1

Identification and Formulation of a Taq DNA Polymerase with Tracers and High Density Reagent A composition conforming to the present invention was developed to facilitate analysis of products resulting from PCR. The composition comprises an essential PCR component, Taq DNA polymerase, with sufficient glycerol to facilitate the application of the reaction product to an agarose gel for electrophoretic analysis. The composition also comprises a red dye that aids in visualization and mixing of the enzyme in the reaction mixture. The red dye also serves as a tracer to follow the progressive movement of PCR products through an agarose gel during electrophoresis. The color red was selected for aesthetic reasons and confers no particular advantage as a tracer.

Figure 6:
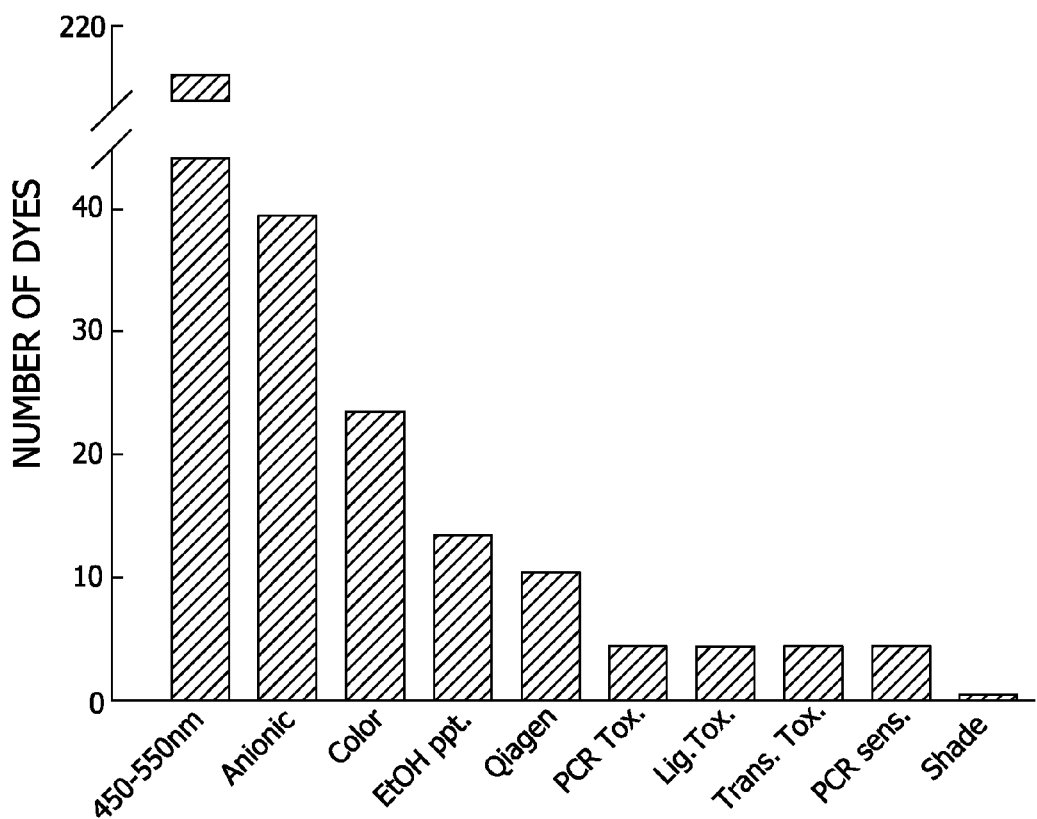
FIG. 6 graphically depicts a dye selection summary according to methods and criterion described in greater detail in Example 1.

FIG. 5 summarizes the steps taken to develop this composition. Since nucleic acid products of PCR are highly anionic, they are applied to the agarose gel near the anode and move toward the cathode as the electrophoresis progresses. Therefore, to be useful as a tracer in electrophoresis the dye molecule is preferably anionic. FIG. 6 is a dye selection summary. The selection process criterion include: 430-570 nm-visible absorption max; anionic-anionic dyes; color not too yellow/orange or purple; EtOH precipitate did not co-precipitate with DNA; chaotropic salt/silica purification (Qiagen PCR columns)-isolated DNA was colorless; PCR toxicity—little impact on $^{32}$P PCR product yield; ligation toxicity—little to no effect on ligation/transformation of EcoRI-pUC19; PCr sensitivity—amplification similar to no dye as a function of template concentration; shade-marketing. From 180+ red dyes (absorbance max between 450 and 570 nm) (Table 1) approximately 40 anionic dyes were selected (Table 2).

TABLE 1

Dyes initially considered

| Dye | $\lambda_{max}$ |
|---|---|
| Bis-N-methylacridinium nitrate | 430 |
| 4-(p-Nitrophenylazo)-resorcinol | 432 |
| Auramine O | 432 |
| Martius Yellow | 432 |
| 3',3",5',5"-Tetraiodophenolsulfonephthalein | 433 |
| 6'-Butoxy-2,6-diamino-3,3'-azodipyridine | 435 |
| Quinoline Yellow A, spirit soluble | 435 |
| m-Cresol Purple, sodium salt | 436 |
| Methyl Red, sodium salt | 437 |
| Methylthymol Blue, water soluble | 438 |
| a-Naphthyl Red | 439 |
| Palatine Fast Yellow BLN | 440 |
| Twort Stain | 440 |
| Pyrocatechol Violet | 441 |
| Acridine Yellow G | 442 |
| Mordant Brown 33 | 442 |
| 2-(5-Bromo-2-pyridylazo)-5-(dimethylamino)phenol | 443 |
| Disperse Orange 3 | 443 |
| Acid Yellow 99 | 445 |
| Thymolphthalein monophosphoric acid, disodium salt hydrate | 445 |
| Acid Orange 51 | 446 |
| Eriochrome Cyanine R | 446 |
| Malachite Green Carbinol base | 446 |
| Ethyl Red | 447 |
| Chrysoidin | 449 |
| Orange G | 475 |
| Sudan I | 476 |
| trans-p-Carotene | 478 |
| Fast Yellow | 480 |
| Pyrogallol Red | 480 |
| Direct Black 22 | 481 |
| Crocein Orange G | 482 |
| Rosolic Acid | 482 |
| Disperse Orange 1 | 483 |
| Eriochrome Red B | 483 |
| Orange 11 | 483 |
| Thorin I | 483 |
| Purpurin | 485 |
| Quinizarin | 485 |
| Mordant Brown 1 | 487 |
| Acridine Orange | 488 |
| Para Red | 488 |
| Acridine Orange | 489 |
| Acid Orange 8 | 490 |
| Astrazon Orange G | 490 |
| Fluorescein diacetate | 490 |
| Fluorescein isothiocyanate, isomer I | 490 |
| Quinalizarin | 490 |
| Tropaeolin 0 | 490 |
| Zincon | 490 |
| Zincon, monosodium salt | 490 |
| Fluorescein, water soluble | 491 |
| Acridine Orange hydrochloride | 492 |
| Mordant Brown 48 | 492 |
| Methyl Red hydrochloride | 493 |
| Sudan 11 | 493 |
| Acid Red 183 | 494 |
| Reactive Orange 16 | 494 |
| Carminic acid | 495 |
| Disperse Red 19 | 495 |
| Fluoresceinamine, isomer 11 | 495 |
| Fluorescein | 496 |
| Fluoresceinamine, isomer I | 496 |
| BrilliantYellow | 497 |
| Congo Red | 497 |
| Acid Red 97 | 498 |
| Cochineal | 498 |
| Arsenazo I | 499 |
| Fluorexon | 499 |
| Benzopurpurin 4B | 500 |
| Mordant Brown 4 | 500 |
| Reactive Red 8 | 500 |
| Acid Alizarin Violet N | 501 |
| Rhodamine 123 dehydrate | 501 |
| Darrow Red | 502 |
| Disperse Red 1 | 503 |

TABLE 1-continued

Dyes initially considered

| Dye | $\lambda_{max}$ |
|---|---|
| Xylidine Ponceau 3RS | 503 |
| Acid Red 106 | 505 |
| Acid Red 88 | 505 |
| Biebrich Scarlet, water soluble | 505 |
| Nuclear Fast Red | 505 |
| Acid Red 4 | 506 |
| New Coccine | 506 |
| 2-(4-Sulfophenylazo)-1,8-dihydroxy-3,6-naphthalene-disulfonic | 507 |
| Direct Red 23 | 507 |
| Merbromin | 507 |
| Methyl Orange | 507 |
| Sudan III | 507 |
| Toluidine Red | 507 |
| Acid Red 4 | 508 |
| Acid Red 8 | 508 |
| Direct Red 81 | 508 |
| 2',7'-Dichlorofluorescein | 509 |
| Brilliant Crocein MOO | 510 |
| Chromotrope 2R | 510 |
| Basic Red 29 | 511 |
| Acid Red 151 | 512 |
| Chromoxane Cyanine R | 512 |
| Quinalizarin | 512 |
| Acid Red 37 | 513 |
| Acid Red 114 | 514 |
| Chromotrope 2B | 514 |
| Eosin B | 514 |
| Eosin Y | 514 |
| Ponceau SS | 514 |
| Acid Red 150 | 515 |
| Chromotrope FB | 515 |
| Acid Red 40 | 516 |
| Azocarmine B | 516 |
| Mordant Blue 9 | 516 |
| Reactive Red 4 | 516 |
| Cibacron Brilliant Red 3B-A | 517 |
| Disperse Red 13 | 517 |
| Eosin Bluish blend | 517 |
| 4,5,6,7-Tetrachlorofluorescein | 518 |
| Bordeaux R | 518 |
| Oil Red 0 | 518 |
| Acid Violet 7 | 520 |
| Methyl eosin | 520 |
| Ponceau S | 520 |
| Rose Bengal, bis(triethylammonium) salt | 520 |
| Sudan IV | 520 |
| Amaranth | 521 |
| Emodin | 521 |
| Eosin Y, free acid | 521 |
| Giemsa Stain | 521 |
| Oil Red EGN | 521 |
| Purpuri'n | 521 |
| Azure A eosinate | 522 |
| Diiodofluorescein | 522 |
| Direct Red 75 | 522 |
| Eosin B, spirit soluble | 522 |
| Jenner Stain | 522 |
| Leishman Stain | 522 |
| May-Grbnwald Stain | 522 |
| Wright Stain | 522 |
| Wright Stain, solution in methanol | 522 |
| Azure B eosinate | 523 |
| Zincon, monosodium salt | 523 |
| Acid Blue 120 | 524 |
| Azure 11 eosinate | 524 |
| Eosin Y lactone | 524 |
| Rhodamine 6G | 524 |
| Tetrachrome Stain (MacNeal) | 524 |
| Erythrosin B | 525 |
| Erythrosin Yellowish blend | 525 |
| Ethidium bromide | 525 |
| Acid Violet 5 | 527 |
| Plasmocorinth B | 527 |
| Eriochrome Blue Black 2B | 528 |
| Quinaldine Red | 528 |
| Rhodamine 6G Perchlorate | 528 |

TABLE 1-continued

Dyes initially considered

| Dye | $\lambda_{max}$ |
|---|---|
| Rhodamine 6G tetrafluoroborate | 528 |
| Sulforhodamine G | 529 |
| Violamine R | 529 |
| Chromotrope 2R | 530 |
| Safranine 0 (Y, T) | 530 |
| Alum Carmine | 531 |
| Carmine | 531 |
| Acid Red 1 | 532 |
| Acid Red 106 | 532 |
| Ethyl Eosin | 532 |
| Arsenazo 111, sodium salt hydrate | 533 |
| Erythrosin B, spirit soluble | 533 |
| Sudan Red 7B | 533 |
| Ruthenium Red | 534 |
| Nuclear Fast Red | 535 |
| Acid Red 40 | 538 |
| Alizarin Violet 3R | 540 |
| Neutral Red | 540 |
| Aluminon | 542 |
| Rhodamine B | 543 |
| Basic Fuchsin | 544 |
| Basic Fuchsin, special for flagella | 544 |
| Pararosaniline base | 544 |
| Rhodamine B base | 544 |
| Acid Fuchsin, calcium salt | 545 |
| Acid Violet 17 | 545 |
| Aurintricarboxylic acid | 545 |
| Aurintricarboxylic acid, trisodium salt | 545 |
| Pararosaniline acetate | 545 |
| Acid Fuchsin, sodium salt | 546 |
| Carbol Fuchsin | 547 |
| Alizarin Blue Black B | 548 |
| Phloxine B | 548 |
| Pyronin Y | 548 |
| Rose Bengal | 548 |
| Basic Fuchsin, biological stain | 549 |
| Direct Violet 51 | 549 |
| 9-Phenyl-2,3,7-trihydroxy-6-fluorone | 552 |
| Bromopyrogallol Red | 552 |
| Phenolphthalein | 552 |
| Rhodanile Blue | 552 |
| New Fuchsin | 553 |
| Nile Red | 553 |
| Pyronin B | 553 |
| Sulforhodamine B | 554 |
| Alizarin Red S monohydrate | 556 |
| Methylene Violet 3RAX | 557 |
| PhenolRed | 557 |
| Rose Bengal, bis(triethylammonium) salt | 559 |
| Arsenazo III | 560 |
| Pinacyanol chloride | 560 |
| Acid Blue 161 | 563 |
| Carmine | 563 |
| Nigrosin, alcohol soluble | 565 |
| Acid Blue 113 | 566 |
| o-Cresolphthalein | 566 |
| Alizarin | 567 |
| Sulfonazo 111, tetrasodium salt | 567 |
| Palatine Chrome Black 6BN | 569 |
| Brilliant Black BN | 570 |
| Cresol Red | 570 |
| Bromocresol Green (also broad absorbance at 417 nm) | 617 |

TABLE 2

Properties of anionic dyes

| No | Dye | $\lambda_{max}$ (nm) | Color | EtOH | Qiagen | 'CR |
|---|---|---|---|---|---|---|
| 1 | Orange G | 475 | X | | | |
| 2 | Acid Red 150 | 515 | | X | | |
| 3 | Acid Red 88 | 505 | solubility | | | |
| 4 | Acid Red 106 | 532 | | | X | |
| 5 | m-Cresol Purple, sodium salt | 436 | X | | | |
| 6 | 2-(4-Sulfophenylazo)-1,8-dihydroxy-3,6-naphthalene-disulfonic acid, trisodium salt | 507 | | | X | |
| 7 | Mordant Blue 9 | 516 | X | | | |
| 8 | Chromotrope 2R | 510 | | | | X |
| 9 | Pyrogallol Red | 480 | | | | X |
| 10 | Reactive Red 4 | 516 | | | | X |
| 11 | Disperse Orange 1 | 483 | X | | | |
| 12 | Congo Red | 497 | X | | | |
| 13 | Direct Red 81 | 508 | | X | | |
| 14 | Phloxine B | 548 | X | | | |
| 15 | Eriochrome Cyanine R | 446 | X | | | |
| 16 | Acid Violet 17 | 545 | X | | | |
| 17 | Chromotrope 2B | 514 | | | X | |
| 18 | Zincon, monosodium salt | 490 | X | | | |
| 19 | Methyl Red, sodium salt | 437 | X | | | |
| 20 | Acid Orange 8 | 490 | X | | | |
| 21 | Rosolic Acid | 482 | solubility | | | |
| 22 | Eosin Y | 514 | X | | | |
| 23 | Bordeaux R | 518 | | | | X |
| 24 | Acid Red 106 | 505 | | | | |
| 25 | Acid Red 4 | 506 | | | | |
| 26 | Acid Red 1 | 532 | | | | |
| 27 | Bromocresol Green (also broad absorbance at 417 nm) | 617 | X | | | |
| 28 | Ponceau S | 520 | | X | | |
| 29 | Benzopurpurin 4B | 500 | solubility | | | |
| 30 | Acid Orange 51 | 446 | X | | | |
| 31 | Amaranth | 521 | | | | |

TABLE 2-continued

Properties of anionic dyes

| No | Dye | $\lambda_{max}$ (nm) | Color | EtOH | Qiagen | 'CR |
|---|---|---|---|---|---|---|
| 32 | 4-(p-Nitrophenylazo0-resorcinol | 432 | X | | | |
| 33 | Biebrich Scarlet, water soluble | 505 | | X | | |
| 34 | Martius Yellow | 432 | X | | | |
| 35 | Reactive Orange 16 | 494 | | | | X |
| 36 | Direct Violet 51 | 549 | X | | | |
| 37 | Chromotrope FB | 515 | | | X | |
| 38 | Direct Red 75 | 522 | X | | | |
| 39 | Acid Violet 5 | 527 | | | | |
| 40 | Acid Red 97 | 498 | | | | X |

Each of these dyes were dissolved in water and those that were not particularly red (i.e. were too yellow/orange or purple), or lacked sufficient solubility, were removed from consideration (Table 2, those marked under "Color").

The 20 dyes which remained were assayed for their ability to be removed from DNA by ethanol precipitation. To 1 µg of lambda DNA enough dye was added to yield a highly colored solution. Addition of two volumes of 3M ammonium acetate, then 6 volumes of ethanol followed. The DNA was pelleted by centrifugation. The appearance of a colored pellet caused the dye to be removed from consideration (FIG. 6, EtOH ppt.; Table 2, those marked under "EtOH"). In the presence of the remaining dyes, one µg quantities of DNA were purified by solid phase extraction on Qiagen PCR product purification columns (Qiagen, Hilden, Germany) according to the manufacturers protocol. Dyes that yielded colored eluants were dropped from consideration (FIG. 6, labeled "Qiagen", Table 2, those marked under column labeled "Qiagen"). The assays performed to this point were done at the onset of the screening because they were the least laborious.

Figure 7:
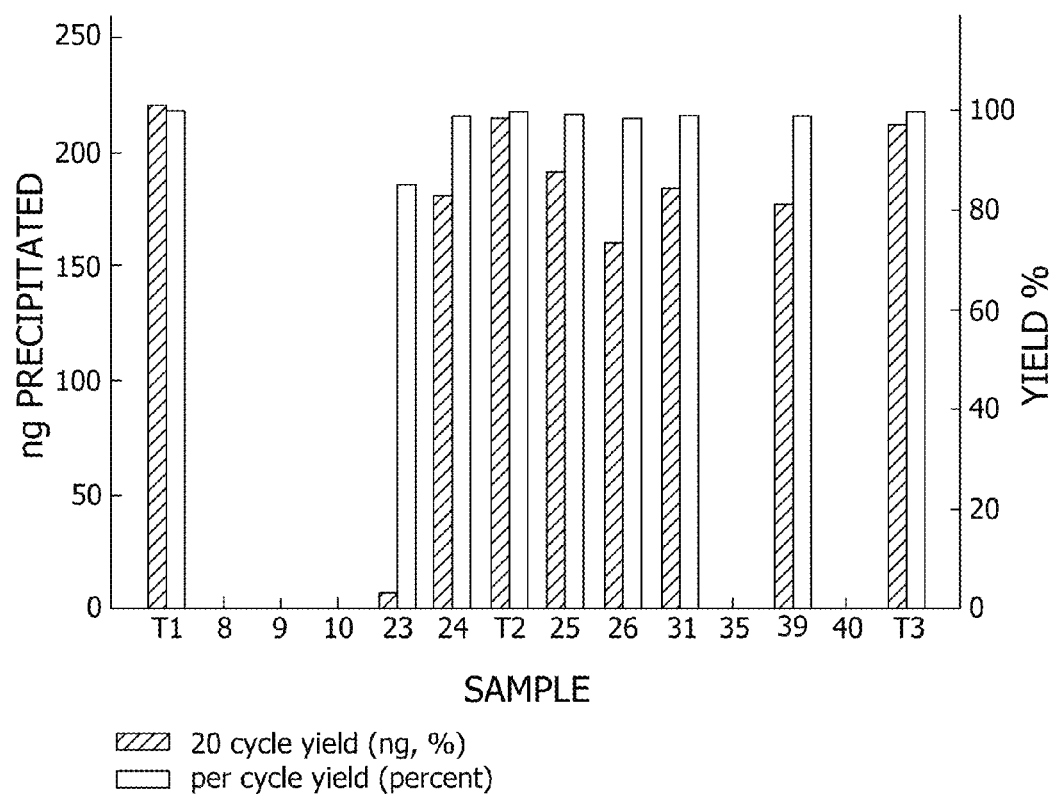
FIG. 7 graphically depicts the results of PCR toxicity experiments performed in Example 1.

The dyes that survived these preceding tests were included in a PCR toxicity study. The dyes were added to PCR reactions at concentrations considered adequate for product performance. Enough of a 2x PCR master mix consisting of Taq DNA polymerase, 0.1 u/µl (Sigma Chemical Co., St. Louis, Mo.), PCR buffer (2x) (Sigma), dNTP's (200 µM each) (Sigma), $\alpha^{32}$PdCTP (Amersham USA, Piscataway, N.J.), target DNA (lambda, 2 ng/µl) (Sigma) and primers (Perkin-Elmer 500 bp control, 2 µM) (Perkin-Elmer, Norwalk, Conn.) was prepared to accommodate all 11 remaining dyes plus three no dye controls. Ten µl of the 2x master mix was dispensed into reaction tubes followed by addition of 10 µl of aqueous darkly colored dye solutions or water (controls). The PCR cycling protocol was 20 cycles of 94/55/72° C. at one minute each. 20 µl of quench solution (50 µg/µl calf thymus DNA, 20 mM EDTA) was added followed by precipitation with 40 µl 40% trichloroacetic acid (TCA)/4% sodium pyrophosphate (NaPPi). The reactions were filtered on glass fiber filters, washed with 5% TCA/2% NaPPi and counted by scintillation methods. This quench/precipitation procedure will henceforth be referred to as "TCA precipitation". As shown in FIG. 7, some dyes significantly inhibited the PCR reaction such that little or no product resulted (i.e. numbers 8, 9, 10, 35 and 40). However, other dyes were relatively inert (i.e. 23, 24, 25, 26, 31, 39). The dyes that inhibited PCR were dropped from consideration (FIG. 6, PCR Tox, Table 2, those marked under "PCR"). Number 23 was dropped because its per cycle yield was substantially lower than the other dyes (FIG. 7). Per cycle yield was calculated assuming the overall yield was the per cycle yield raised to the 20$^{th}$ power (FIG. 7). In FIG. 7, T1, T2, and T3 represent Taq controls (no dye) as in block and precipitation, numerals are dye number. Per cycle yield is calculated assuming $y^{20}=y_1^{20}$ where y is the 20 cycle yield (measured) and $y_1$ is the per cycle yield. Table 3 summarizes the results as graphically depicted in FIG. 7 for each of dyes 23, 24, 25, 26, 31, and 39.

TABLE 3

DNA Yield by Dye

| Dye | $Y^{(20\%)}$ | $Y^{1(\%)}$ |
|---|---|---|
| 23 | 9.04 | 85.3 |
| 24 | 84.1 | 99.1 |
| 25 | 88.9 | 99.4 |
| 26 | 74.6 | 98.5 |
| 31 | 85.6 | 99.3 |
| 39 | 82.4 | 99.0 |

Figure 8:
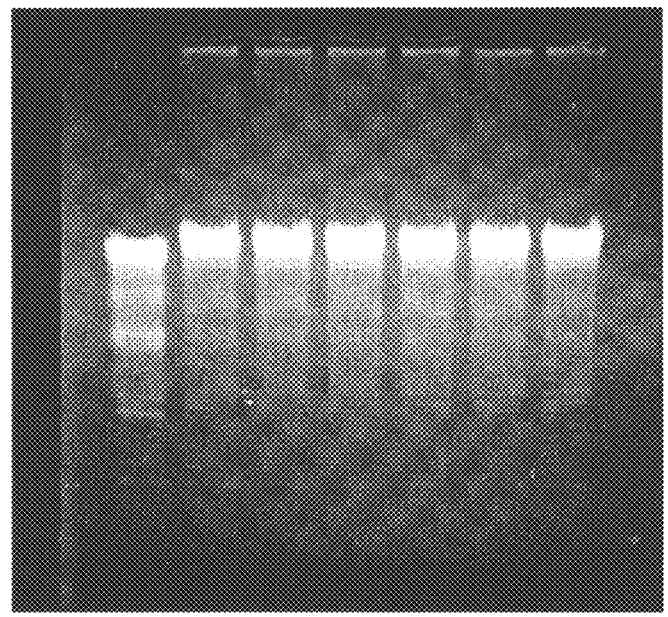
FIG. 8 is a gel depicting the results of a toxicity screen performed on dyes selected according to experiments performed in Example 1.
Figure 9:
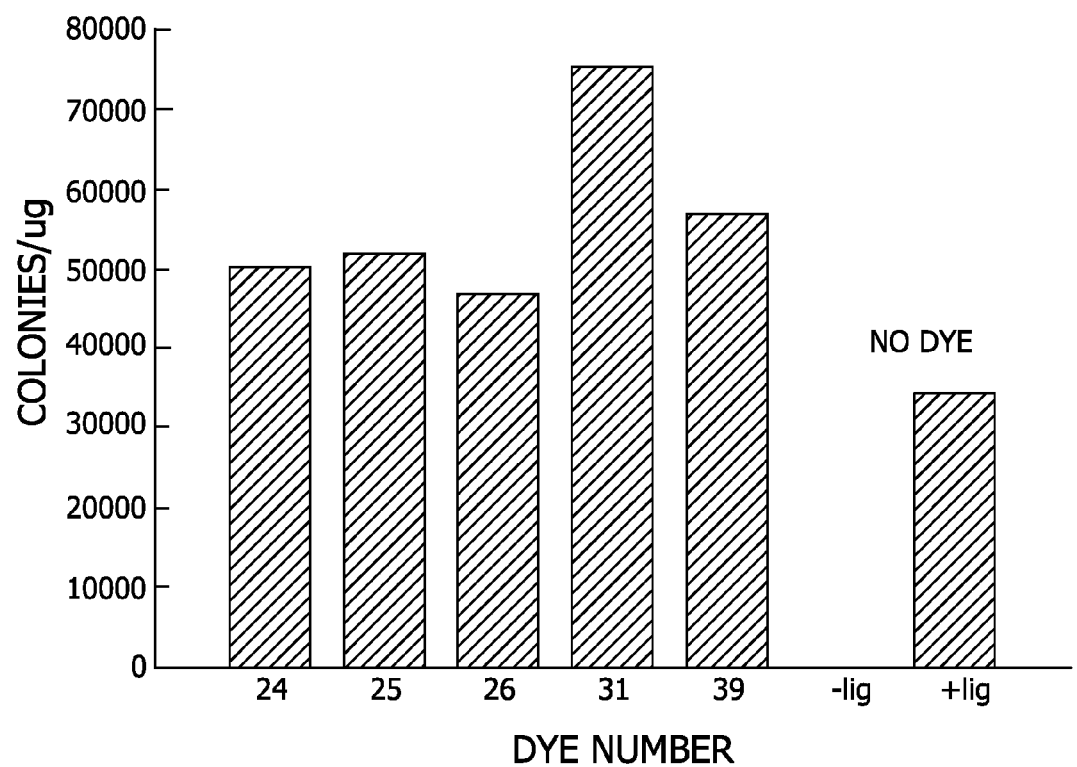
FIG. 9 graphically depicts the transformation efficiency of dyes in a ligation/transformation protocol according to experiments performed in Example 1.

The dyes which remained after the PCR toxicity screen were further screened for their toxicity on ligation and transformation, two downstream procedures often carried out using unpurified PCR products. As shown in FIG. 8, ligation in the presence of the remaining dyes (24, 25, 26, 31 and 39 lanes 3-7 respectively) was equivalent to the no dye control (lane 2). Lane 1 is a control which had no ligase. Ligations were carried out as described in the figure legend. The same dyes were also tested for suitability in a ligation/transformation protocol. Transformation efficiency was not compromised by the presence of dye (FIG. 9). Increased efficiencies, as evidenced in the figure, were not investigated. The experiment was performed as summarized in the figure legend.

Figure 10:
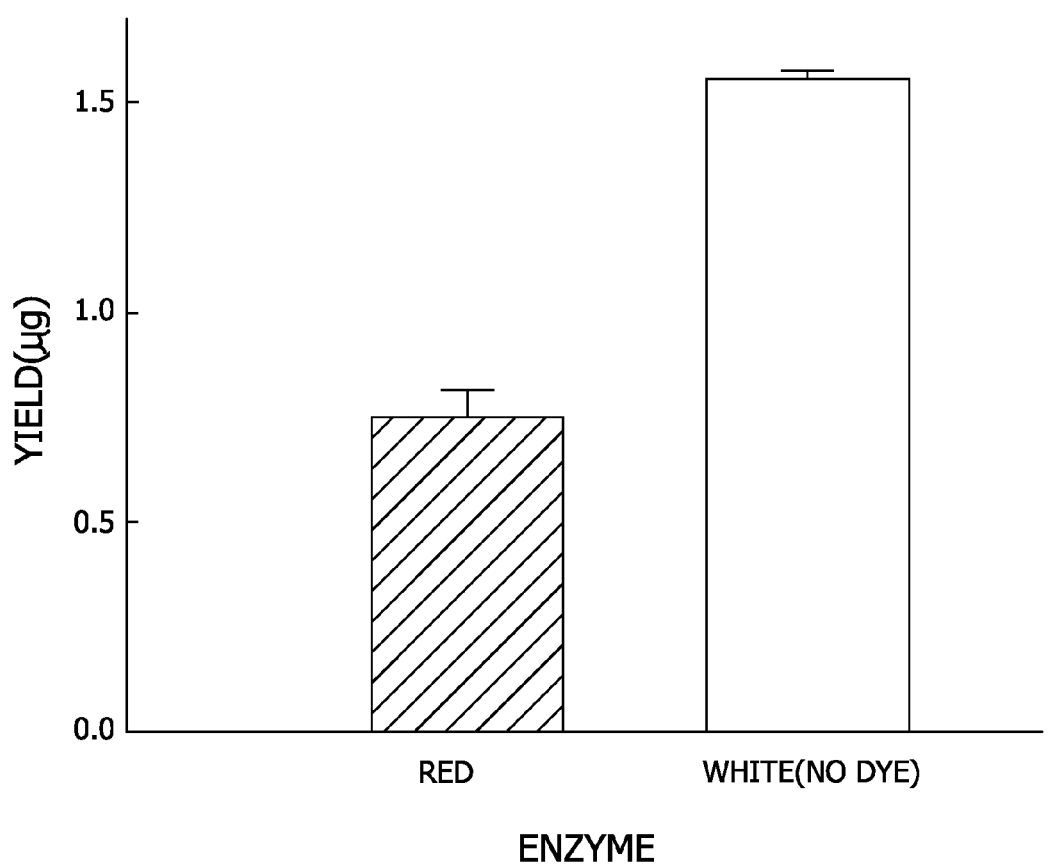
FIG. 10 graphically depicts the results of the use of a tracer dye from Example 1 in a PCR reaction according to experiments performed in Example 1.

On the basis of performance to this point, the remaining dyes were considered substantially equivalent as tracer candidates. Acid violet 5 (number 39, Table 2) was chosen as a possible finalist candidate. Using this dye in a reaction mix at an absorbance of 10 (at its absorbance maximum of 527 nm) a PCR reaction was performed. The inclusion of this dye in a reaction mix resulted in a minimum of 50% loss (relative to the same reaction without the dye) in PCR product yield (FIG. 10) as measured by TCA precipitation. This was considered unacceptable, but was overcome by further development efforts.

Figure 11:
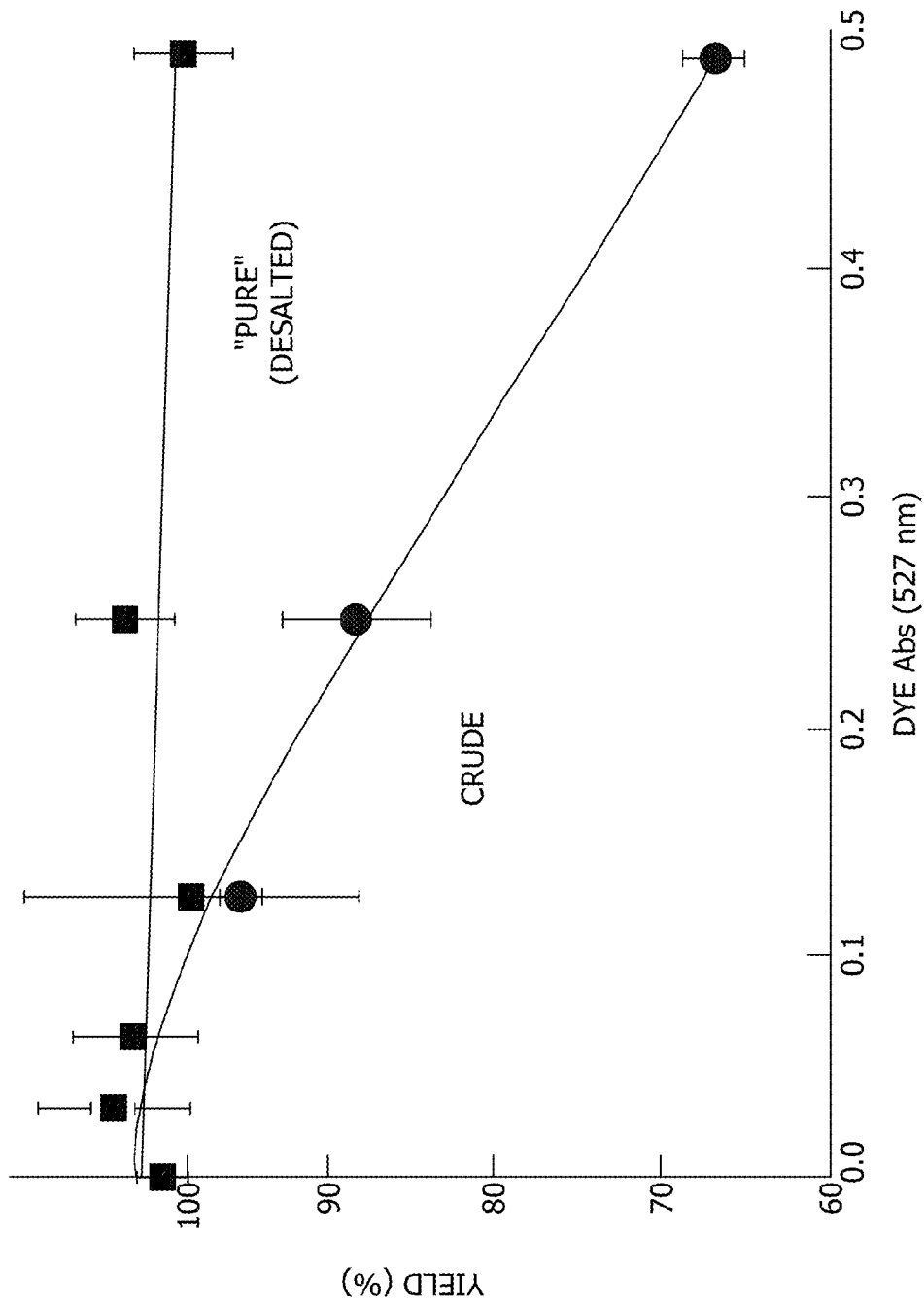
FIG. 11 graphically depicts the results of a comparison of crude to pure (desalted) dyes on PCR yields according to experiments performed in Example 1.
Figure 12A:
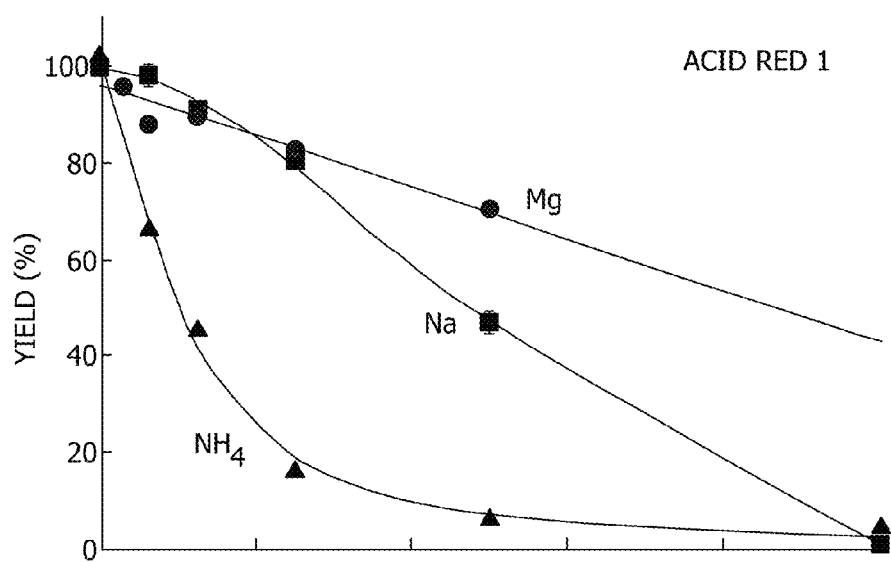
Figure 12B:
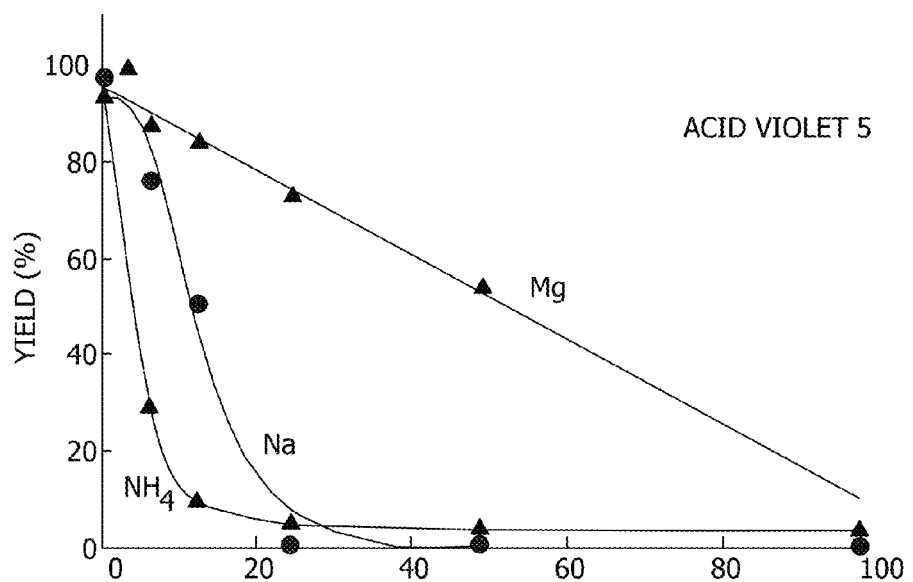

In general, the available dyes, as well as those investigated, are derived from unrelated applications. That is, many are used as fabric dyes, food colorings, biological stains etc. As such, they are available in various states of purity. In the case of the finalists, they all had purities of 80% or less, as determined by the product labels. In further experiments, PCR yields (determined by TCA precipitation) in reactions containing various concentrations of acid violet 5 (determined by $A_{527}$) were compared before and after purification of the crude dye by reverse phase desalting. PCR product yield was much less susceptible to dye concentration for the desalted compound relative to the crude compound (FIG. 11). Since reversed phase desalting is not an attractive method for large scale dye purification, acid precipitation followed by ammonium hydroxide dissolution/evaporation to produce the ammonium dye was investigated. This procedure should result in an essentially salt free product. These procedures (reversed phase desalting and acid/ammonium hydroxide) were carried out for acid red 1 (No. 26, Table 2) and acid violet 5 (No. 39). It was found that the ammonium dyes were more PCR toxic than the sodium (i.e. desalted) dyes (FIGS. 12A and 12B). The dyes were converted to their magnesium salts to further characterize the effect of counterion identity. This was accomplished by addition of magnesium chloride (excess) to a solution of the crude dye. The magnesium dye that immediately precipitated was recrystallized from water. As shown in FIGS. 12A and 12B, the Mg salts of both acid red 1 (FIG. 12A) and acid violet 5 (FIG. 12B) were much less toxic to PCR than either the sodium or ammonium salts. In analogy with the magnesium salts, the calcium and zinc salts of acid red 1 were prepared to investigate whether the effect was divalent vs. monovalent cation or cation identity specific. FIG. 12C demonstrates that the magnesium salt was least toxic. From these data it was concluded that the dye was likely sequestering magnesium from the PCR reaction which caused decreased product yields.

Figure 13A:
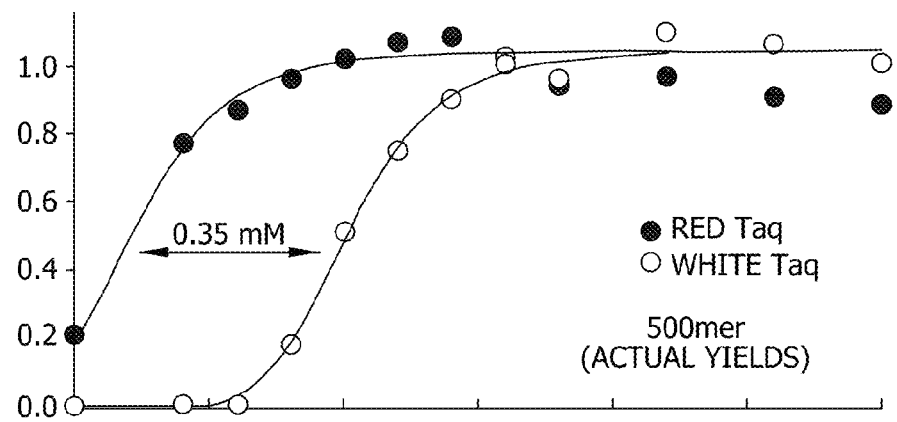
FIGS. 13A-13C graphically depict the results of tests performed to determine the concentration of free $Mg^{+2}$ contributed by the dyes to PCR reactions according to experiments performed in Example 1.
Figure 13B:
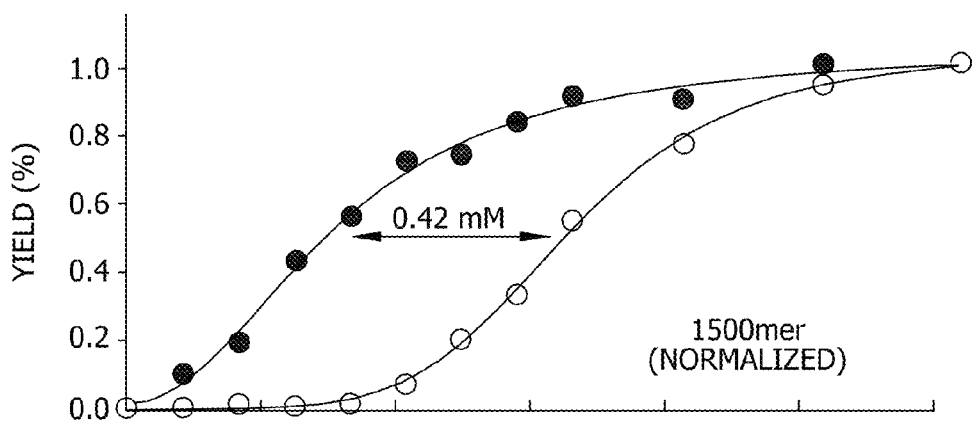
Figure 13C:
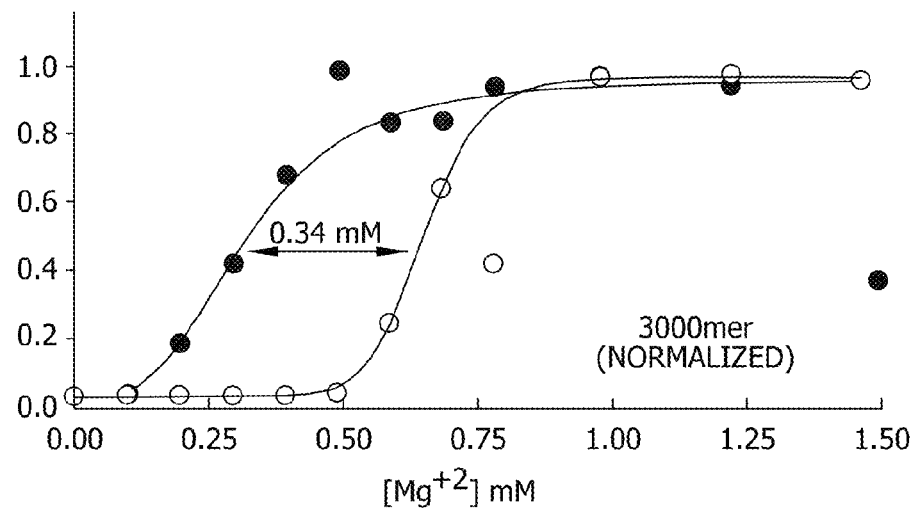

A dye formulation of the magnesium salts of 80% acid red 1/20% acid violet 5 was created (percentages based on absorbance at the wavelength of each dye's maximum absorbance [acid red 1=531 nm, acid violet 5=528 nm]). That particular ratio was used for aesthetic reasons, however any ratio, or either of the dyes individually would be similarly effective. To further investigate the effects of $Mg^{++}$, since the dye is supplying magnesium to a magnesium dependent reaction (i.e. PCR), free $Mg^{+2}$ concentration contributed by the dye to the reaction was determined. This was determined by varying the magnesium concentration in dye containing vs. dye free reactions in a dose response manner. FIGS. 13A-13C show that for products ranging from 500 to 3000 bp, the difference between red and white Taq at the midpoint of the magnesium concentration titrations is approximately 0.4 mM (0.37+/−0.04). The 10× buffer usually supplied with Taq was reformulated to account for this perturbation (i.e. the concentration of $MgCl_2$ was changed from 15 to 11 mM in the 10× buffer).

A preferred composition was formulated at 1 u/µl Taq polymerase in Taq storage buffer (consisting of 20 mM Tris-HCl, pH 8.0, 100 mM KCl, 0.1 mM EDTA, 1 mM DTT, 0.5% TWEEN® 20 (polyoxyethylenesorbitan monolaurate), 0.5% IGEPAL® CA-630 (octylphenoxy poly(ethyleneoxy) ethanol), 50% glycerol in water) with the magnesium formulation of dye at a total absorbance of 300. The dye composition was 80% acid red 1, 20% acid violet 5 (100%=absorbance of acid red 1 at $\lambda_{max}$+absorbance of acid violet 5 at $\lambda_{max}$; absorbance of acid red 1=240, acid violet 5=60). This formulation is designated "REDTAQ™". When added to a PCR reaction mixture at 0.05 u/µl Taq, the total dye absorbance is 15. The dye combination at this concentration was visible in a subsequent agarose gel electrophoresis of the completed reaction mix, yet the combination was relatively non-toxic to PCR. A lower concentration of the dye in the reaction mixture would be difficult to see during a subsequent agarose gel electrophoresis. As a comparison, the previously discussed prior art Taq-dye formulation, RED HOT® DNA Polymerase, has an absorbance of 3.3 at 572 nm, and 4.6 at 435 nm. At the recommended concentration in a PCR reaction mixture, RED HOT® DNA Polymerase has an absorbance of 0.033 and 0.046, at 572 and 435 nm, respectively. Therefore, in contrast to REDTAQ™, the RED HOT® DNA Polymerase formulation would not be useful as a tracer in an electrophoretic analysis of a PCR reaction.

Figure 14:
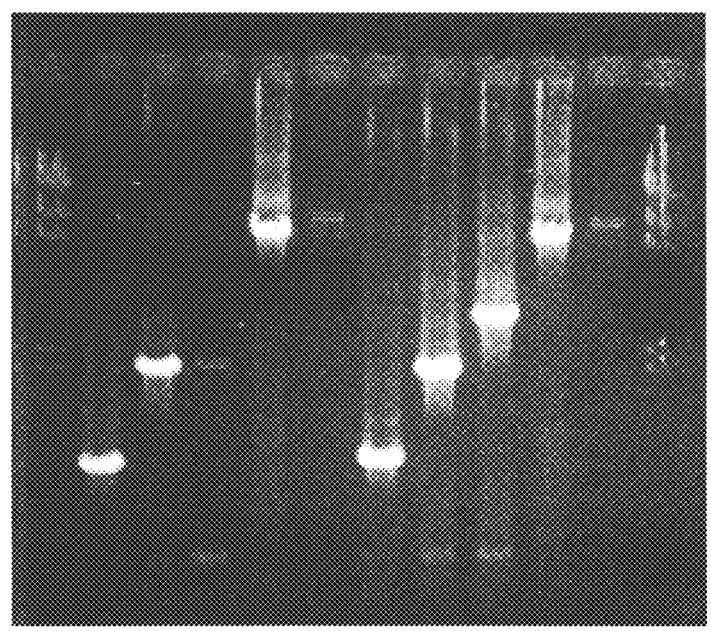
FIG. 14 is a gel depicting the results of a comparison of PCR products prepared using the REDTAQ™ formulation with 10× buffer (with 11 mM $MgCl_2$) as described in Example 1 with conventional Taq/10× buffer (with 15 mM $MgCl_2$).
Figure 15:
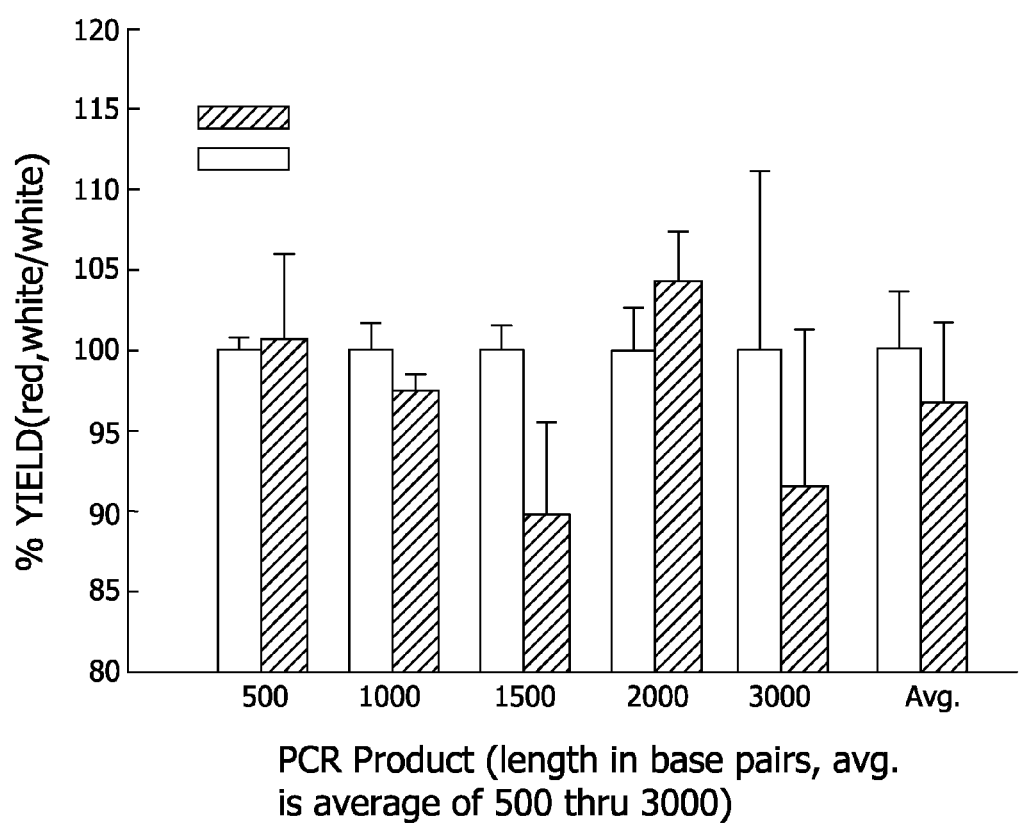
FIG. 15 graphically depicts the results of tests comparing the PCR product yield using the REDTAQ™ formulation described in Example 1 with conventional PCR yield using conventional Taq. (Target=λ)
Figure 16:
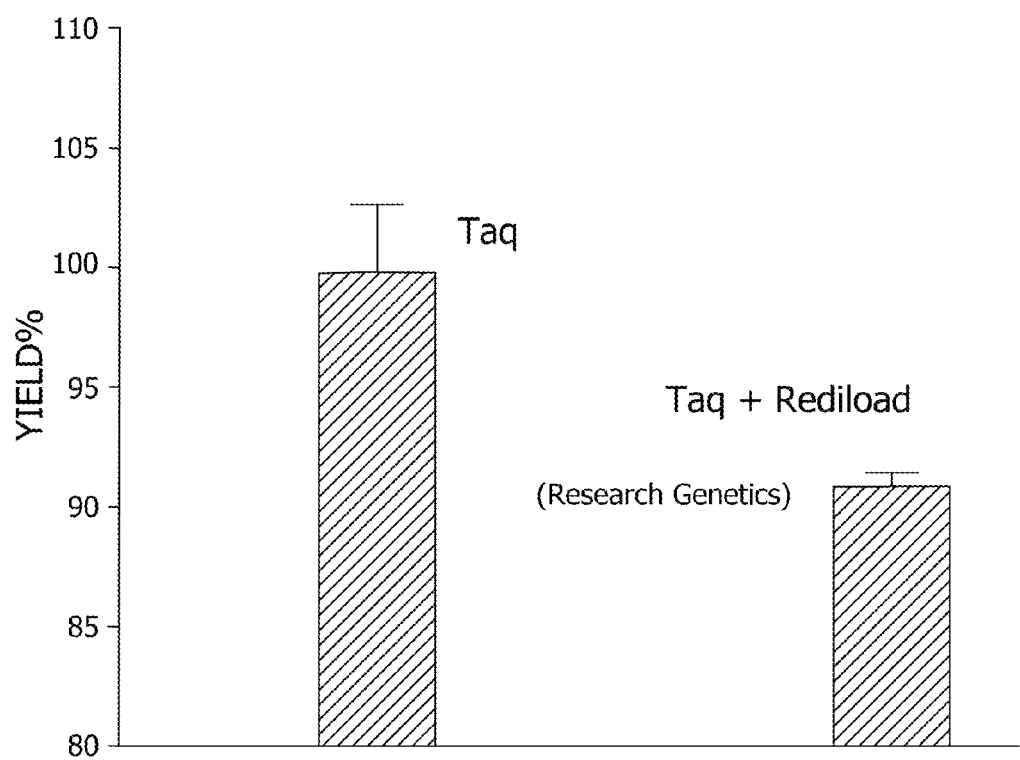
FIG. 16 graphically depicts the results of tests comparing the PCR product yield using Taq™ and Taq™ plus REDI-LOAD™ according to experiments performed in Example 1.

PCR products prepared using the REDTAQ™ formulation with the 10× buffer described above (with 11 mM $MgCl_2$) were compared with conventional Taq/10× buffer (with 15 mM $MgCl_2$). FIG. 14 shows a 1% agarose gel of amplification products resulting from this comparison. From the gel it is apparent that the amplifications using REDTAQ™ were equivalent to those using Taq without dye. The exception to this is amplification of the 3 kb fragment, where the amplification with conventional Taq failed for unknown reasons (Lane 4). However, when product yields were compared for a variety of target sizes (FIG. 15), both conventional Taq and REDTAQ™ did effectively amplify a 3 kb target. In that comparison, product yield was not compromised by REDTAQ™. When a similar comparison was made with REDILOAD™, a commercial formulation of a red loading buffer (without an essential reaction component) which is added before a PCR reaction, the REDILOAD™ product reduced PCR product yield by approximately 10% (FIG. 16), relative to the same reaction without REDILOAD™.

EXAMPLE 2

Determination of the Compatibility of a Dye with Restriction Endonucleases

Figure 17:
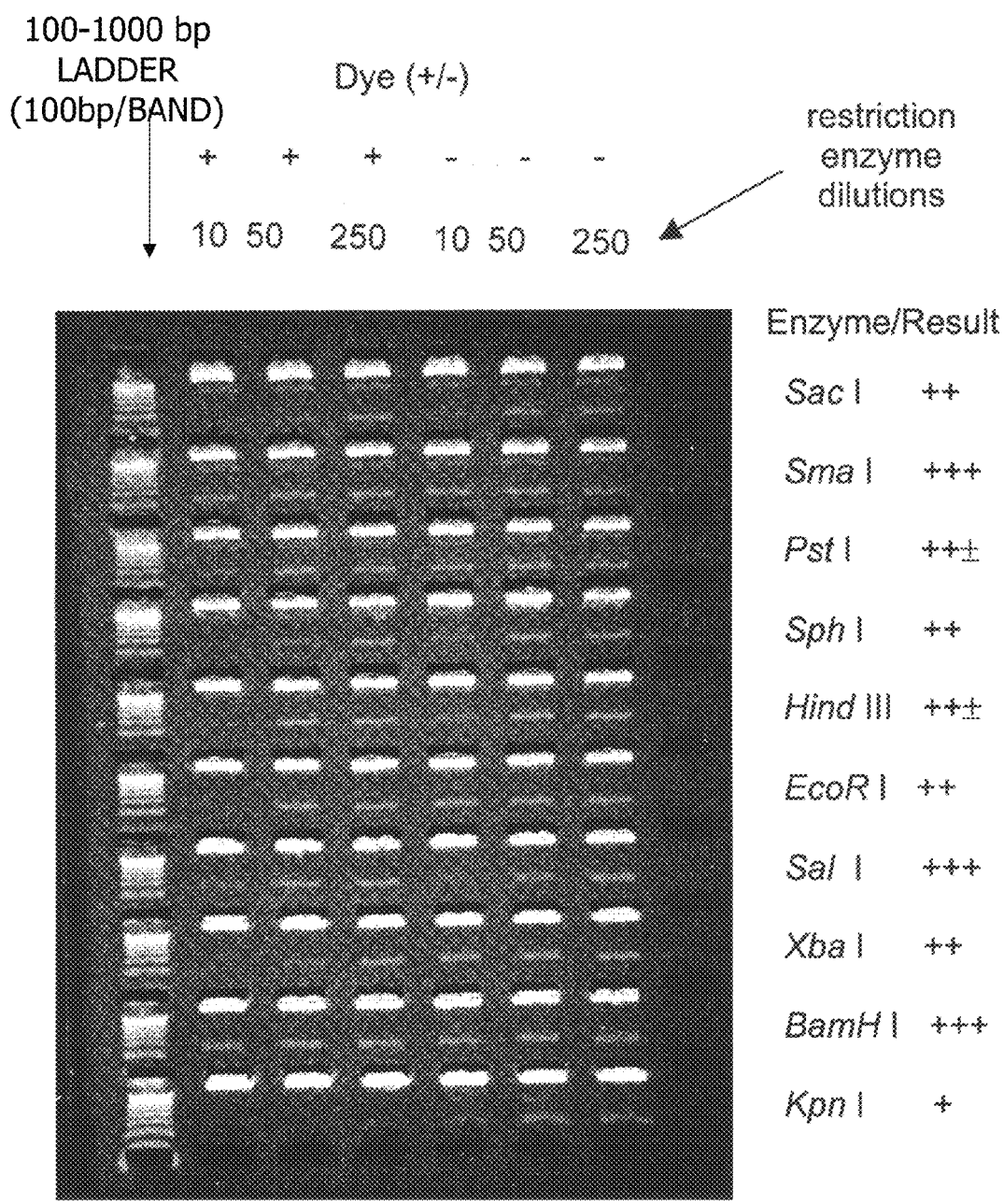
FIG. 17 is a gel depicting the results of an experiment comparing the effectiveness of various restriction enzymes with and without the presence of a dye as described in greater detail in Example 2.

The effectiveness of restriction enzymes in cutting target DNA when a dye is present in the reaction mixture was evaluated. A variety of restriction enzymes were assayed for the detrimental effect of adding Amaranth (No. 31, Table 2) to a restriction digest as assayed by agarose gel electrophoresis. NdeI-cut pUC19 plasmid was prepared. This linearized plasmid was then digested with one of several restriction enzymes which normally cut pUC19 at a polylinker site. Thus, each enzyme would be expected to yield a product of similar sizes (ranging from 212 to 263 bp). The restriction enzyme digests were performed in the presence, or absence, of Amaranth dye, and at various concentrations of the enzyme. The results of this experiment are shown in FIG. 17. Column 1 (the leftmost column) contains 100 bp molecular weight ladders. Columns 2-4 contains cleavage products from sequential 5-fold dilutions of the restriction enzymes in the presence of dye. Columns 5-7 are as columns 2-4 but without dye. Columns 2 and 5 contained the restriction enzyme at $\frac{1}{10}^{th}$ the suppliers concentration (i.e. the enzyme was considered a 10× concentration). The buffers used for the digests were as recommended by the supplier. The enzymes used are listed along the right side of the gel. The relative susceptibility of the enzyme to the dyes' presence is reported next to the enzyme. The sizes of the small bands in the electrophoresis runs range from 212 to 263 bp. The larger, brighter bands contain the full length NdeI-cut pUC19 (2686 bp) and/or the larger fragment of the NdeI-cut pUC19 which was also cut with the test enzyme (2423-2474 bp). +++equals inert, blank is completely toxic. This preliminary experiment reveals that the restriction enzymes tested were relatively insensitive to dye addition. That is, with the exception of KpnI, Amaranth was relatively inert in these reactions. This experiment was conducted using commercially prepared (crude) dye (dye content approximately 90%). Based on the previously discussed results with Taq polymerase, a dye screening and possible cleanup/counterion exchange, similar to that used in Example 1, should result in the discovery of a dye system that would work for a majority of restriction enzymes.

To enable direct gel loading, the restriction digest would have to contain a component that made the solution denser than the electrophoresis buffer. Like the PCR product, glycerol or another high density agent should suffice. Generally, star activity (alternate site cutting of DNA due to high glycerol content) can occur at glycerol concentrations above 5%. For REDTAQ™, solutions as low as 1.5% glycerol were effective as a high density agent. Thus, it is clearly possible that restriction digest reagents could be formulated to contain enough glycerol or other density increasing solutes to allow for direct gel loading.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. An aqueous reagent for an ex-vivo polymerase reaction, the reagent comprising Taq DNA polymerase, an anionic tracer dye selected from the group consisting of acid violet 5, acid red 1, acid red 106, acid red 4, a salt of any one thereof, and combinations of acid violet 5 and acid red 1, the anionic tracer dye being unbound to primer or nucleotides, and a solute to increase the physical density of the reagent, wherein the anionic tracer is present in the reagent in an amount sufficient to be visible for a post-polymerase reaction analysis, the reagent being free of primers and nucleic acid polymer template and having a physical density of at least 1.01 g/cm$^3$, but less than the density of the solute.

2. The reagent of claim 1, wherein the reagent has a physical density of at least 1.1 g/cm$^3$, but less than the density of the solute.

3. The reagent of claim 1, wherein the reagent has a physical density of 1.14 g/cm$^3$.

4. The reagent of claim 1, wherein the solute comprises glycerol, trimethylglycine, or sugar.

5. The reagent of claim 1, wherein the concentration of Taq polymerase in the reagent is 0.033 to 10 units/μl.

6. An aqueous reagent for use in forming a polymerase reaction mixture comprising a Taq DNA polymerase, a nucleic acid polymer template, primers, nucleotides, a visually detectible anionic tracer dye selected from the group consisting of acid violet 5, acid red 1, acid red 106, acid red 4, a salt of any one thereof, and combinations of acid violet 5 and acid red 1, the anionic tracer dye being unbound to primer or nucleotides, and a solute to increase the physical density of the reagent, the reagent comprising the Taq DNA polymerase, the detectible anionic tracer dye present in an amount sufficient to be visible in a chromatographic or electrophoretic procedure, and the solute, but being free of primers and the nucleic acid polymer template, the reagent having a physical density of at least 1.01 gm/cm$^3$, but less than the density of the solute.

7. The reagent of claim 6, wherein the reagent has a physical density of at least 1.1 g/cm$^3$, but less than the density of the solute.

8. The reagent of claim 6, wherein the reagent has a physical density of 1.14 g/cm$^3$.

9. The reagent of claim 6, wherein the concentration of Taq polymerase in the reagent is 0.033 to 10 units/μl.

10. The reagent of claim 6, wherein the solute comprises glycerol, trimethylglycine, or sugar.

* * * * *